US010271503B2

(12) United States Patent
Assouline et al.

(10) Patent No.: US 10,271,503 B2
(45) Date of Patent: Apr. 30, 2019

(54) RESISTANCE TO GEMINIVIRUSES IN WATERMELONS

(71) Applicant: VILMORIN & CIE, Paris (FR)

(72) Inventors: Yael Assouline, Rehovot (IL); Eran Yossov, M.P. Ashkelon Coast (IL); Smadar Shoval, Ashdod (IL)

(73) Assignee: VILMORIN & CIE, Paris (FR)

( * ) Notice: Subject to any disclaimer, the term of this patent is extended or adjusted under 35 U.S.C. 154(b) by 154 days.

(21) Appl. No.: 15/119,672

(22) PCT Filed: Feb. 20, 2015

(86) PCT No.: PCT/EP2015/053668
§ 371 (c)(1),
(2) Date: Aug. 17, 2016

(87) PCT Pub. No.: WO2015/124753
PCT Pub. Date: Aug. 27, 2015

(65) Prior Publication Data
US 2017/0006791 A1 Jan. 12, 2017

(30) Foreign Application Priority Data
Feb. 21, 2014 (EP) .................................. 14305244

(51) Int. Cl.
*A01H 5/08* (2018.01)
*A01H 5/10* (2018.01)
*A01H 6/34* (2018.01)
*A01H 1/04* (2006.01)
*C12Q 1/6895* (2018.01)

(52) U.S. Cl.
CPC ............... *A01H 6/342* (2018.05); *A01H 1/04* (2013.01); *A01H 5/08* (2013.01); *A01H 5/10* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

PUBLICATIONS

International Search Report and Written Opinion of the International Searching Authority in connection with PCT International Application No. PCT/EP2015/053668.
European Search Report in connection with European Patent Application No. EP 14 30 5244.
Abudy, A., et al., "Watermelon chlorotic stunt and Squash leaf curl begomoviruses—New threats to cucurbit crops in the Middle East", Israel Journal of Plant Sciences, Laser Pages Publishing, Jerusalem, Israel, vol. 58, No. 1, Jan. 1, 2010, pp. 33-42.
Bananej, K., et al., "Host range of an Iranian isolate of Watermelon chlorotic stunt virus as determined by whitefly-mediated inoculation and agroinfection, and its geographical distribution", J. Phytopathol., 150:423-430, 2002.
Bumgarner, N. R. and Kleinhenz, M., "Using Brix as an Indicator of Vegetable Quality: Instructions for Measuring Brix in Cucumber, Leafy Greens, Sweet Corn, Tomato and Watermelon", Department of Horticulture and Crop Science, The Ohio State University, HYG-1653-12, 2012.
Lapidot, M. and Friedmann, M., "Breeding for resistance to whitefly-transmitted geminiviruses", Ann. Appl. Biol. 140:109-127, 2002.
Raaed M. Mohamed Elhassan, et al., "Evaluation of Watermelon (*Citrullus* spp.) germplasm for resistance to Watermelon Chlorotic Stunt Virus", Sudan Journal of Agricultural Research, vol. 12, pp. 87-94, 2008.
Yousif, M. T., et al., "Sources of resistance to Watermelon Chlorotic Stunt Virus in melon", Plant Breeding, 126:422-427, 2007.
El-Jack, A. E., et al., "Evaluation of watermelon (*Citrullus* spp.) germplasm for resistance to watermelon chlorotic stunt virus", Internet Citation, 2009, retrieved from the Internet: URL: http://agris.fao.org/agris-search/search.do?recordID=SD2009000073 [retrieved on Jul. 7, 2014].
Mohamed Taha Yousif, et al., "Morphological Veriability and Phenotypic Association among Pairs of Characters of some Watermelon chlorotic stunt virus Resistant Lines of Citrullus lanatus Thunb", Cucurbit Genetics Cooperative Report, n°35/36, Jan. 1, 2012, pp. 7-10.
Mohamed, et al., "Breeding watermelon (*Citrullus lanatus*) for resistance to water melon chlorotic stunt virus disease [Sudan]" Internet Citation, 1997, retrieved from the Internet: URL: http://agris.fao.org/agris-search/search.do?recordID=SD1997000256 [retrieved on Jul. 7, 2014].
Karen R. Harris; et al., "Isolation Sequence Analysis, and Linkage Mapping of Nucleotide Binding Site—Leucine-rich Repeat Disease Resistance Gene Analogs in Watermelon", Journal of the America Society for Horticultural Science, Nov. 1, 2009, pp. 649-657.
Guner, N., et al., "Overview of Potyvirus resistance in watermelon 1", May 17, 2008.
Levi, et al., "An Extended Genetic Linkage Map for Watermelon Based on a Testcross and a BC2F2 Population", American Journal of Plant Sciences, vol. 2, 2008, pp. 93-110, Jun. 2011.

*Primary Examiner* — Elizabeth F McElwain
(74) *Attorney, Agent, or Firm* — John P. White; Cooper & Dunham LLP

(57) ABSTRACT

The present invention is directed to watermelon plant and seed, namely of C. lanatus, which are resistant to geminiviruses, especially to begomoviruses including WmCSV, comprising in their genome introgressed sequences from C. colocynthis conferring resistance to said viruses, when present homozygously. The introgressed sequences are preferably characterized by defined alleles of SNPs on chromosome 6. The introgressed sequences can be chosen from those present in the genome of a plant of Citrullus lanatus—WMCSVR accession number NCIMB 42197. The invention is also directed to parts of these resistant plants, as well as progeny, to the use of these plants for introgressing the resistance in another genetic background, as well as to different methods for obtaining resistant watermelon plants or seeds.

23 Claims, No Drawings
Specification includes a Sequence Listing.

RESISTANCE TO GEMINIVIRUSES IN WATERMELONS

CROSS-REFERENCE TO RELATED APPLICATIONS

This application is a § 371 national stage of PCT International Application No. PCT/EP2015/053668, filed Feb. 20, 2015, claiming priority of European Patent Application No. EP 14305244.7, filed Feb. 21, 2014, the content of each of which is hereby incorporated by reference into the application.

REFERENCE TO A SEQUENCE LISTING

This application incorporates by reference nucleotide and/or amino acid sequences which are present in the file named "160817_88839_Substitute_Sequence_Listing_CAE.txt", which is 7.00 kilobytes in size, and which was created Aug. 16, 2016 in the IBM-PC machine format, having an operating system compatibility with MS-Windows, which is contained in the text file filed Aug. 17, 2016 as part of this application.

The present invention relates to resistance and/or tolerance in plants of *Citrullus lanatus* to geminiviruses, especially to begomoviruses, inter alia to Watermelon Chlorotic Stunt Virus (WmCSV). According to the invention, the resistance is provided by DNA sequences, introgressed from *Citrullus colocynthis* at specific loci in the genome of a *Citrullus lanatus* plant. The introgressed sequences can be present homozygously or heterozygously in the genome of *Citrullus lanatus*, and when they are present homozygously, they confer resistance to said viruses.

BACKGROUND OF THE INVENTION

*Citrullus lanatus* (commonly known as watermelon) is a plant native to southern Africa, believed to have originated in areas near Namibia, Botswana, and Zimbabwe (Wein, H. C. 1997). Thanks to its sweet red-fleshed fruit, watermelon has become a popular summer food throughout the world. According to Food and Agriculture Organization (FAO, 2011), world production of watermelon exceeded 104 million tons. Watermelon is a member of the cucurbitaceae family that also comprises cucumbers, squashes (including pumpkins), luffas, gourds and melons.

There are four recognized *Citrullus* species, *C. lanatus, C. colocynthis, C. rehmii* and *C. ecirrhosus*; all have 22 chromosomes and can be crossed with each other successfully. *C. lanatus* is an annual species. It has large, broad green leaves. Fruits are of medium to large size, with thick rind and solid flesh with high water content. Flesh color may be red, yellow, or white.

*C. colocynthis* is a perennial watermelon. It differs from *C. lanatus* primarily in the size of plant organs. Leaves are small with narrow lobes, and are hairy and grayish in color. Bloom is profuse in autumn, when fresh vegetative growth also occurs. Fruits are small, not exceeding 5-10 cm in diameter, with rind and spongy flesh that are always bitter.

A variety of pathogens affect the productivity of watermelon plants including viruses fungi, bacteria, nematodes, and insects (Larson et al., 2000). Watermelons are inter alia susceptible to many viruses and virus resistance is therefore of major agricultural importance (Prowidenti, 1993).

The taxonomic family Geminiviridae includes some of the most important plant viruses causing severe diseases in agricultural, ornamental and horticultural crops. Geminiviruses generally are characterized by the unique twin shape of a fused icosahedral viral particle. Geminiviruses are plant viruses which have ambisense single-stranded circular DNA genomes. The genome can either be a single component of 2500-3000 nucleotides, or two similar-sized components. They generally have an elongated, geminate capsid with two incomplete T=I icosahedra joined at the missing vertex. The capsids range from 18-20 nm in diameter with a length of about 30 nm. Viruses with bipartite genomes (begomoviruses only) have these components separated into two different particles, therefore more than one virus particle is required to infect a cell. Transmission of these viruses can be via leafhoppers (mastreviruses, curtoviruses) or via species of whitefly (begomoviruses) or via treehoppers (topocuviruses).

The geminiviruses are responsible for a significant amount of crop damage worldwide. Diseases caused by these viruses have long been recognized as a limitation to the cultivation of several important crops, including maize, cassava, bean, squash, cucurbits, and tomato. Epidemics of geminivirus diseases have arisen due to a number of factors, including the recombination of different geminiviruses co-infecting a plant, which enables novel, possibly virulent viruses to be developed. Other contributing factors include the transport of infected plant material to new locations, expansion of agriculture into new growing areas, and the expansion and migration of vectors that can spread the virus from one plant to another.

Geminiviruses comprise a large and diverse family of viruses that infect a wide range of important monocotyledonous and dicotyledonous crop species and cause significant yield losses. Geminiviruses are classified into four genera: genus *Mastrevirus* (e.g., Maize streak virus), genus *Curtovirus* (e.g., Beet curly top virus), genus *Begomovirus* (e.g., SLCV), and genus *Topocuvirus* (Tomato pseudo-curly top virus).

The genus *Begomovirus* contains more than 200 viral species (Fauquet et al, 2008) and belong to the taxonomic family Geminiviridae. They are plant viruses that as a group have a very wide host range. Natural hosts of begomoviruses are plant species in which the virus can replicate, cause systemic infection, and encapsidate, and from which virions are ingested and transmitted to a susceptible host by the whitefly vector (Funayama, 2001). Worldwide they are responsible for a large amount of economic damage to many important agronomic and horticultural crops such as tomatoes, beans, squash, cassava and cotton in subtropical and tropical regions of Americas, Africa and Asia. Morphologically, *begomovirus* particles are non-enveloped. The nucleocapsid is 38 nm long and 15-22 nm in diameter. While particles have basic isocahedral symmetry, they consist of two incomplete icosahedra—missing one vertex—joined together. There are 22 capsomeres per nucleocapsid. *Begomovirus* species has single stranded closed circular DNA. Most begomoviruses have a bipartite genome, meaning that the genome is segmented into two segments (referred to as DNA A and DNA B) that are packaged into separate particles. Both segments are generally required for successful symptomatic infection in a host cell, but DNA B is dependent for its replication upon DNA A, which can in some begomoviruses apparently cause infections on its own.

Watermelon Chlorotic Stunt Virus (WmCSV), a *begomovirus*, can cause severe losses in cucurbits, as its host range includes all the major cultivated cucurbit crops: melon (*Cucumis melo*), squash, cucumber (*Cucumis sativus* L.), pumpkin (*Cucurbita maxima* Duchesne), and tropical pumpkin (*C. moschata* Duchesne) (Jones, D. R. 2003, Lapidot, M. and Friedmann, M., 2002), however, WmCSV affects mostly watermelon plants.

The virus was first identified in Yemen in 1986 (Bedford, I. D. et al. 1994, and Jones, P. et al, 1988, and Walkey, D. G. A. et al, 1990) and later reported from Sudan (Lecoq, H. et al, 1994, Marchelo, P. W., 1996), Iran (Bananej, K. et al., 2002), Israel (Abudy, A. et al., 2010, and M. S. Ali-Shtayeh, R. M. et al, 2012), Jordan and Lebanon (Al-Musa, A. et al., 2011, Samsatly, J. et al., 2012).

Infected watermelon plants develop vein yellowing, chlorotic mottling, and severe stunting of young leaves followed by a substantial fruit yield loss (Bananej et al., 2002; Jones et al., 1988).

Current methods of preventing and controlling geminiviruses include controlling the spread of insect vectors that carry the virus, developing transgenic plants expressing the viral coat protein, and using classical breeding methods to develop plants having natural resistance to the virus. Disease resistant plants developed using classical plant breeding offer an effective, safe, and relatively less expensive method of controlling many crop diseases.

Different levels of tolerance to WmCSV were observed in *Citrullus lanatus* landraces from Sudan; there is however no report of resistance as such in these landraces, and no result regarding transmission of this tolerance to commercial lines.

A tolerance to Watermelon Chlorotic Stunt Virus (WmCSV) was also identified years ago in *Citrullus colocynthis* PI 494529 (Raaed M. Elhassan et al., 2008), but it was identified as a dominant one which was further not simply inherited and whereas minor genes could be involved. As such, its use for breeding resistant watermelon varieties may prove difficult and possibly lead to losses of levels of resistance. No data regarding successful introgression of this tolerance into watermelon varieties is reported in the literature.

Resistance to WmCSV was also identified in another related genus, namely *Cucumis melo* (Yousif, M, T et al, 2007). No intergenic transmission of this trait from *Cucumis melo* to *Citrullus lanatus* has however been obtained so far.

In spite of intensive work in this respect and the importance of watermelon production worldwide, currently, no *C. lanatus* watermelon plants resistant or tolerant to WmCSV have been obtained through introgression of the trait from a wild *citrullus* accession or from another related genus. This failure can be attributed to probable undesirable negative traits linked to the resistance found in other species or genus, which are hard or impossible to break, especially traits of flesh qualities (color, brix, fibers), it has thus not been possible up to now to introgress a form of WmCSV resistance while simultaneously retaining the traits of flesh qualities. Another reason for the failure to obtain resistant *C. lanatus* watermelon plants might come from the genetic mechanism of the previously identified source of resistance—namely a complex source with minor genes, as reported in Raaed M. Elhassan et al., 2008.

Therefore, there is an important need in the art to identify a reliable monogenic source of resistance and/or tolerance which could then be easily used to obtain resistant commercial plants of *Citrullus lanatus*.

The present invention provides *Citrullus lanatus* watermelon plants that display resistance and/or tolerance to Watermelon Chlorotic Stunt Virus (WmCSV) and to the other geminiviruses, as well as methods that produce or identify *Citrullus lanatus* watermelon plants that display resistance and/or tolerance to Watermelon Chlorotic Stunt Virus (WmCSV) and other geminiviruses. The present invention also discloses molecular genetic markers, especially SNPs, linked to the recessive genetic locus conferring resistance and/or tolerance to geminiviruses.

SUMMARY

The present inventors have identified a wild *Citrullus colocynthis* which displays a high level of resistance to WmCSV and they have been able to introgress, into *Citrullus lanatus* genetic background, the *Citrullus colocynthis* sequences conferring resistance to geminiviruses, including resistance to WmCSV, thus obtaining resistant *Citrullus lanatus* plants. The resistance of the present invention is imparted by the newly discovered sequences conferring resistance, said resistance being of monogenic and recessive nature; such that said resistance is easily transferable to different genetic background, due to its monogenic nature, and is unlinked to negative traits, especially unlinked to negative commercial traits such as poor flesh qualities.

The present invention provides introgressed sequences from *Citrullus colocynthis* conferring, when present in the homozygous state, the phenotype of resistance/tolerance to geminiviruses; meaning that the resistance/tolerance phenotype according to the invention is monogenic. The invention also provides *C. lanatus* watermelon plants that display important resistance to geminiviruses, including resistance to WmCSV, as well as methods that produce or identify *C. lanatus* watermelon plants or populations (germplasm) that display resistance to geminivirus infection, as well as seeds, fruits and other plant parts such as pollen and ovules containing the introgressed sequences conferring the resistance. The present invention also discloses molecular genetic markers, especially SNPs, linked to the introgressed sequences conferring resistance, i.e. to the resistance locus also called resistance gene, which is of recessive nature.

Definitions

Flesh color evaluation: the flesh color of the *citrullus* plants is evaluated using RHS (Royal Horticultural Society) color chart (http://www.rhsshop.co.uk). The color is ranked using 5 levels: 1. White—37B, 2. Light pink—39B, 3. Pink—50B, 4. Red—41A, 5. Deep red—44A. The flesh color of the *C. colocynthis* plants carrying the WmCSV resistance, used by the inventors, is white, 37B.

Flesh Firmness evaluation: the flesh firmness is evaluated using a penetrometer. The scale varies from 0.5 (very soft) to 5 (very hard). The values for commercial *C. lanatus* watermelons are usually ranging from 2 to 3. The flesh firmness of the *C. colocynthis* plants carrying the WmCSV resistance identified by the inventors is 5.

Flesh Fiber evaluation: the flesh fiber evaluation is done by the breeder on a scale from 1 to 5, where 1 corresponds to absence of fibers in the flesh, 2 is very little fiber content, 3 is half flesh and half fibers, 4 is very little flesh, mostly fibers and 5 is only fibers, with no flesh at all. The flesh fiber of the *C. colocynthis* plants carrying the WmCSV resistance identified by the inventors is 5, only fibers without any flesh.

Taste evaluation: Fruit taste is subjectively estimated by the breeder by tasting the fruit flesh. The fruit taste is ranked on a scale of 1-5 (1—bitter; 2—bland; 3—mild sweetness; 4—sweet; 5—very sweet). The taste of the *C. colocynthis* plants carrying the WmCSV resistance identified by the inventors is 1, bitter. Other measures are used to assess and describe different aspects of sweetness, such as the measurement of soluble solid content (SSC, or Brix; Bumgarner and Matthew Kleinhenz, 2012).

The term "Resistance" is as defined by the ISF (International Seed Federation) Vegetable and Ornamental Crops Section for describing the reaction of plants to pests or pathogens, and abiotic stresses for the Vegetable Seed Industry.

Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure.

The term 'Tolerance' is used herein to indicate a phenotype of a plant wherein disease-symptoms remain absent upon exposure of said plant to an infective dosage of virus, whereby the presence of a systemic or local infection, virus multiplication, at least the presence of viral genomic sequences in cells of said plant and/or genomic integration thereof can be established. Tolerant plants are therefore resistant for symptom expression but symptomless carriers of the virus. Sometimes, viral sequences may be present or even multiply in plants without causing disease symptoms.

Susceptibility: The inability of a plant variety to restrict the growth and development of a specified pest or pathogen.

A *C. lanatus* plant susceptible to geminiviruses, and especially to WmCSV, is for example the commercially available plant Malali from Hazera Genetics Ltd, now Hazera Seeds Ltd. All commercially available varieties of *C. lanatus* are, to date, susceptible to geminiviruses, inter alia to WmCSV, before the present invention.

A plant according to the invention has thus at least improved resistance to geminiviruses, and especially to WmCSV with respect to the plant Malali, and more generally with respect to any commercial variety of watermelon.

As used herein, the term "offspring" or "progeny" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "heterozygote" refers to a diploid or polyploid individual cell or plant having different alleles (forms of a given gene or sequences) present at least at one locus.

As used herein, the term "heterozygous" refers to the presence of different alleles (forms of a given gene or sequences) at a particular locus.

As used herein, the terms "homolog" or "homologue" refer to a nucleic acid or peptide sequence which has a common origin and/or functions similarly to a nucleic acid or peptide sequence from another species.

As used herein, the term "homozygote" refers to an individual cell or plant having the same alleles at one or more loci on all homologous chromosomes.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "locus" (plural: "loci") refers to any site that has been defined genetically. A locus may be a gene, or part of a gene, or a DNA sequence, and may be occupied by different sequences. A locus may also be defined by a SNP (Single Nucleotide Polymorphism), or by several SNPs.

The *C. lanatus* watermelon plants of the present invention are resistant to geminiviruses; especially to WmCSV; the invention encompasses plants of different ploidy levels, whether a diploid plant, a triploid plant, a tetraploid plant, etc. In some embodiments, the plant is an allopolyploid plant. Such ploidy level is of importance as according to the National Watermelon Promotion Board 68% of the watermelons sold in the United States in 2003 were seedless. This trend has likely been growing as consumer preference continues to shift towards seedless watermelon. Seedless watermelons are triploid hybrids produced by crossing diploid (2×) lines containing 22 chromosomes per cell with tetraploid (4×) lines containing 44 chromosomes per cell. This results in seeds that produce triploid (3×) plants with 33 chromosomes and are thus sterile "seedless fruits". The man skilled in the art of plant breeding will know how to produce *Citrullus lanatus* watermelon plants of the present invention of different ploidy levels, for example through the use of chemicals and/or physical treatments known to induce chromosome doubling in plant cells. For example, colchicine, nitrous oxide gas, heat treatment, amiprophos methyl, trifluralin, oryzalin, and pronamide have been used to obtain progenies with doubled chromosome number in many plant species. A protocol for obtaining seedless watermelon fruits is disclosed in detail in example 8 of the experimental section.

By introgression, it is meant the infiltration of the genes or of genomic sequences of one species into the gene pool of another one from an initial interspecific hybrid between these species.

A variety is a taxonomic nomenclature rank in botany, below subspecies, but above subvariety and form.

DETAILED DESCRIPTION OF THE INVENTION

The present invention is directed to *C. lanatus* watermelon plants that display important resistance to geminiviruses, including resistance to WmCSV, as well as methods that produce or identify *C. lanatus* watermelon plants that display resistance to geminiviruses infection. The present invention also discloses molecular genetic markers, especially SNPs, linked to the resistance loci.

It is to be noted that, whereas the phenotype of interest according to the invention is mainly referred to, in the present description, as "resistance" to geminiviruses, the invention is directed to resistance and/or tolerance to geminiviruses, insofar as, depending on the infection specific conditions, both phenotypes may be observed on the plants. In any case, for the plants of the invention, there are however at least some infection conditions in which the phenotype can be classified as resistance according to the ISF definition given above.

The seeds and plants according to the invention have been obtained from an initial interspecific cross between a plant of *Citrullus colocynthis* COLO1, the introgression partner displaying the phenotype of interest, and a plant of the line *Citrullus lanatus* LANA1, the recurrent susceptible parent. Seeds of *C. lanatus*, from F3 families (phenotyped in example 4 of the experimental section) deriving from this initial interspecific cross, homozygously resistant to geminiviruses, called *Citrullus lanatus*—WMCSVR, have been deposited by the inventors at the NCIMB under the accession number NCIMB 42197 on 5 Dec. 2013. The plants grown from these deposited seeds are plants resistant to geminiviruses, especially resistant to WmCSV, and have moreover a red flesh color.

According to a first aspect, the present invention is thus directed to a *C. lanatus* plant or seed, which is resistant and/or tolerant to geminiviruses, comprising in its genome introgressed sequences or interval from *C. colocynthis* conferring said resistance and/or tolerance to geminiviruses. Said sequences introgressed from *C. colocynthis* confer the resistance to a *C. lanatus* plant or seed only when present homozygously in the *C. lanatus* genome, i.e. when inter alia 2 copies are present on the 2 homologous chromosomes for a diploid plant, when 4 copies are present on the 4 homologous chromosomes for a tetraploid plant, etc. . . . .

The introgressed interval acts as a single recessive allele of a resistance gene responsible for the phenotype (i.e. the resistance trait is monogenic); the F1 generation arising from a cross between a resistant plant and a susceptible plant will thus not display the desired phenotype of geminivirus resistance. Only a plant homozygous for the introgressed interval will fully exhibit the geminivirus resistance phenotype. This phenotype can be used to identify progeny that are homozygous for the claimed introgressed sequences or interval. As mentioned above, the resistance phenotype may, under certain circumstances, be also qualified as tolerance to geminiviruses. The introgressed interval acting as a resistance gene confers the phenotype of interest and is unlinked to negatives features incompatible with marketability of the plants or fruit.

The introgressed sequences are preferably to be found on chromosome 6 in the *C. lanatus* genome and thus confer resistance and/or tolerance to geminiviruses when they are present on every homologous chromosomes 6. The introgressed sequences conferring the resistance and/or tolerance are more preferably located within the chromosomal region of chromosome 6 which is delimited on one side by the SNP#10 (SEQ ID No:10), and on the other side by the telomere of said chromosome 6, wherein said chromosomal region comprises the SNP#1 (SEQ ID No: 1). The telomere, being a region of defined repetitive nucleotide sequences at each end of a chromatid, can indeed be used as a marker of the ends of the chromosome. Since there is a telomere at each extremity of the chromosome, there are two fragments of chromosome 6, delimited on one side by SNP#10 and on the other side by a telomere, but only one comprises the SNP#1, namely the chromosomal region between SNP#10 and the telomere adjacent to SNP#1.

The specific polymorphisms corresponding to the SNPs (Single Nucleotide Polymorphism) referred to in this description, as well as the flanking sequences of these SNPs in the *C. lanatus* genome, are given in the experimental section (see tables 2 and 3) and accompanying sequence listing. Their location in the 1st watermelon genome sequence built is indicated in tables 2 and 3, and their flanking sequences are also illustrated in tables 2 and 3. The introgressed sequences or interval conferring the resistance or tolerance are preferably chosen from the introgressed sequences from *C. colocynthis* present in the genome of a plant of *Citrullus lanatus*—WMCSVR, representative seeds of which are deposited at the NCIMB under the accession number NCIMB 42197. They are especially chosen from the introgressed sequences from *C. colocynthis* present on chromosome 6 of said *Citrullus lanatus*—WMCSVR. Indeed, the deposited seeds comprise, on every homologous chromosomes 6, introgressed sequences from *Citrullus colocynthis* COLO1, i.e. from the introgression partner displaying the phenotype of interest, wherein said introgressed sequences are also conferring the phenotype in *C. lanatus* genetic background. A sample of this *Citrullus lanatus*—WMCSVR seed has been deposited by Hazera Genetics Ltd, now Hazera Seeds Ltd, Berurim, M. P. Shikmim 79837, Israel, pursuant to, and in satisfaction of, the requirements of the Budapest Treaty on the International Recognition of the Deposit of Microorganisms for the Purposes of Patent Procedure (the "Budapest treaty") with the National Collection of Industrial, Food and Marine Bacteria (NCIMB), (NCIMB Ltd, Ferguson Building, Craibstone Estate, Bucksburn, Aberdeen AB21 9YA, United Kingdom), on 5 Dec. 2013, under accession number NCIMB 42197. The deposited seeds are not from a plant variety.

A deposit of this *Citrullus lanatus*—WMCSVR seed is maintained by Hazera Genetics Ltd, now Hazera Seeds Ltd, Berurim, M. P. Shikmim 79837, Israel.

The sequences conferring the resistance are present on every homologous chromosomes 6 of all deposited seeds; as such the genome of these deposited seeds thus represent a reservoir of introgressed sequences from *C. colocynthis* in the *C. lanatus* genome conferring resistance to viruses according to the invention. A plant or seed of the invention comprises in its genome introgressed sequences from *Citrullus colocynthis* which are chosen from this reservoir. Whereas all deposited seeds possess an introgressed fragment at the same locus and conferring the phenotype according to the invention, this introgressed fragment may slightly vary in length between the seeds.

The present invention is thus also directed to a *C. lanatus* seed or plant having in its genome introgressed sequences from *C. colocynthis* conferring resistance to geminiviruses, wherein said introgressed sequences conferring the resistance are chosen from the introgressed sequences from *C. colocynthis* present in the genome of a seed of *Citrullus lanatus*—WMCSVR corresponding to NCIMB 42197 deposit. Preferably, such a resistance is conferred only when said sequences are present homozygously. Said introgressed sequences or intervals may form part of larger introgression fragments from *C. colocynthis* into the genome of a *C. lanatus* plant of the invention.

By "introgressed sequences or intervals from *C. colocynthis* at a given locus" or "introgressed sequences or intervals from *C. colocynthis* present/found at a given locus", it is to be understood that the genomic interval found at this given locus has the same sequence as the corresponding genomic interval found in the *C. colocynthis* donor, i.e. in the introgression partner, at the same locus and also the same sequence as the corresponding genomic interval found in the *Citrullus lanatus*—WMCSVR (NCIMB 42197) at the same locus. By having the "same sequence", it means that the two sequences to be compared are identical to the exception of potential point mutations which may occur during transmission of the genomic interval to progeny, i.e. preferably at least 99% identical on a length of 1 kbase. It can be deduced that a genomic interval under test has the same sequence, in the sense of the invention, as the corresponding genomic interval found in the *C. colocynthis* donor at the same locus, if said genomic interval under test is also capable of conferring resistance to WmCSV. The presence of introgressed sequences into the genome of a *C. Lanatus* plant, seed or cell may for example be shown by GISH (genetic in situ hybridization). GISH is indeed a powerful technique for detection of the introgression of chromatin material from one species onto another species. The advantage of GISH is that the introgression process is visualized by means of 'pictures of the introgressed genome'. With this technique, it is also possible to establish if a particular region of the genome is homozygous or heterozygous, thanks to the use of molecular cytogenetic markers which are co-dominant. By this technique, it is also possible to determine in which chromosome an introgressed gene of interest is present. According to a preferred embodiment, the introgressed sequences conferring the resistance, and which are also to be found in the genome of the deposited seeds, are introgressed on chromosome 6 of a *C. lanatus* plant according to the invention, and more precisely within the chromosomal region of chromosome 6 which is delimited on one side by the SNP#10 (SEQ ID No:10), and on the other side by the telomere of said chromosome 6, wherein said chromosomal region comprises the SNP#1 (SEQ ID No: 1). In other words, in the genome of a *C. lanatus* plant or seed of the invention, the section on chromosome 6 within the region delimited on one side by the SNP#10 (SEQ ID No:10), and on the other side by the telomere of said chromosome and comprising the SNP#1 (SEQ ID No: 1), comprises sequences which are of *C. colocynthis* origin. These sequences are responsible for the geminivirus resistance, in both *C. colocynthis* and *C. lanatus* genetic background.

According to a preferred embodiment, the introgressed sequences present in the genome of a plant or seed of the invention are to be found at one or more of the following loci:

locus encompassing SNP#3 (SEQ ID No:3); and/or
locus encompassing SNP#9 (SEQ ID No:9).

It is noted in this respect that specific positions in a chromosome can indeed be defined with respect to single nucleotide polymorphism, insofar as the flanking sequences of said SNPs are defined. The present inventors have used SNPs, identified by their flanking sequences, present both in *C. lanatus* and *C. colocynthis* genomes, to discriminate between introgressed and endogenously residing sequences and to track down the introgressed sequences from *C. colocynthis* in the *C. lanatus* genome.

The present inventors have identified that introgressed sequences essential for the phenotype of interest, i.e. resistance and/or tolerance are to be found in the vicinity of the SNP#3 or in the vicinity of SNP#9, or in the vicinity of both SNPs. Preferably the introgressed sequences from *Citrullus colocynthis* are to be found in a locus encompassing the position of SNP#3, or in a locus encompassing the position of SNP#9, or in a locus encompassing both the position of SNP#3 and the position of SNP#9. It is to be noted that the loci of SNP#3 and SNP#9 are located within the chromosomal region defined above, i.e. delimited on one side by the SNP#10 (SEQ ID No:10), and on the other side by the telomere of said chromosome and comprising the SNP#1 (SEQ ID No: 1).

When the introgressed sequences from *Citrullus colocynthis* conferring the resistance (or tolerance, depending on the conditions) are found in a locus encompassing SNP#3, then the allele of SNP#3 is the allele of SNP#3 found in the wild *Citrullus colocynthis* introgression partner COLO1 and also in the deposited resistant *Citrullus lanatus*—WMCSVR, i.e. allele C of SNP#3 (SEQ ID No:3). The 5' flanking region of SNP#3, or the 3' flanking region of SNP#3, or both regions, are also identical to *C. colocynthis* sequences in this region. Therefore, the SNP#3 may form part of the 3' border or 5' border of the introgressed interval, or may be within the introgressed interval conferring the desired phenotype.

When the introgressed sequences from *Citrullus colocynthis* conferring the resistance (or tolerance, depending on the conditions) are found in a locus encompassing SNP#9, then the allele of SNP#9 is the allele of SNP#9 found in the wild *Citrullus colocynthis* introgression partner COLO1 and also in the deposited resistant *Citrullus lanatus*—WMCSVR, i.e. allele C of SNP#9 (SEQ ID No:9). The 5' flanking region of SNP#9, or the 3' flanking region of SNP#9, or both regions, are also identical to *C. colocynthis* sequences in this region. Therefore, the SNP#9 may form part of the 3' border or 5' border of the introgressed interval, or may be within the introgressed interval conferring the desired phenotype.

When the introgressed sequences from *Citrullus colocynthis* conferring the resistance are found in a locus encompassing both SNP#3 and SNP#9, then the alleles of these SNPs are allele C of SNP#3 and allele C of SNP#9. The presence of the introgressed sequences of interest can indeed be revealed by the presence of specific alleles of given SNPs, wherein said alleles are characteristic of the introgression partner, and distinct from the allele of the recurrent *C. lanatus* parent for these SNPs. The alleles of given SNPs can thus reflect the presence of the introgression sequences of the invention. These alleles are inter alia allele A of SNP#1 (SEQ ID No:1), allele G of SNP#2 (SEQ ID No:2), allele C of SNP#3, allele T of SNP#4 (SEQ ID No:4), allele C of SNP#5 (SEQ ID No:5), allele G of SNP#6 (SEQ ID No:6), allele C of SNP#7 (SEQ ID No:7) and allele C of SNP#9. Allele G of SNP#2 (SEQ ID No:2), allele C of SNP#3, allele T of SNP#4 (SEQ ID No:4), allele C of SNP#5 (SEQ ID No:5), allele G of SNP#6 (SEQ ID No:6), allele C of SNP#7 (SEQ ID No:7) and allele C of SNP#9 correspond to the alleles of these SNPs found in the deposited seeds NCIMB 42197.

According to another embodiment, the introgressed sequences present in the genome of a plant or seed of the invention are to be found at one or more of the following loci:

locus encompassing SNP#1 (SEQ ID No:1);
locus encompassing SNP#2 (SEQ ID No:2);
locus encompassing SNP#4 (SEQ ID No:4);
locus encompassing SNP#5 (SEQ ID No:5);
locus encompassing SNP#6 (SEQ ID No:6); and/or
locus encompassing SNP#7 (SEQ ID No:7);

in addition or in place of the introgressed sequences found at the locus encompassing SNP#3 and/or SNP#9 according to the previous embodiment.

According to a preferred embodiment, introgressed sequences from *Citrullus colocynthis* are to be found at the loci encompassing SNP#3, SNP#4, SNP#5, SNP#6, SNP#7 and SNP#9. Preferably, introgressed sequences from *Citrullus colocynthis* are also found at the loci encompassing SNP#1 and SNP#2. Most preferably, introgressed sequences are to be found at the loci encompassing SNP#2, SNP#3, SNP#4, SNP#5, SNP#6 and SNP#9.

Consequently, a resistant plant or seed of the invention may also be characterized by the homozygous allele C of SNP#3, or homozygous allele C of SNP#9, or both; preferably by the homozygous allele C of SNP#3. They may also be characterized in addition by at least one of the following alleles: allele A of SNP#1 (SEQ ID No:1), allele G of SNP#2 (SEQ ID No:2), allele T of SNP#4 (SEQ ID No:4), allele C of SNP#5 (SEQ ID No:5), allele G of SNP#6 (SEQ ID No:6) and allele C of SNP#7 (SEQ ID No:7).

The presence of the introgressed sequences can also be revealed by genic amplification of sequences in the proximity of the SNPs defined in the present invention, especially SNP#3 and SNP#9 and comparison with the sequence of the respective amplification fragment, obtainable by carrying out the amplification on seeds deposited at the NCIMB under accession number NCIMB 42197. Primers for the genic amplification can be defined by use of the flanking sequences disclosed in the present invention, potentially in combination with the available *Citrullus lanatus* genome assembly.

Preferably, the introgressed sequences conferring the phenotype of interest, i.e. resistance or tolerance, are in linkage disequilibrium with the allele of SNP#3, or with the allele of SNP#9, or with both the alleles of SNP#3 and SNP#9. According to a preferred embodiment, the allele of SNP#3 is "C". According to a further embodiment, the allele of SNP#9 is "C". According to the preferred embodiment, the alleles of both SNP#3 and SNP#9 are "C" and are in linkage disequilibrium with the introgressed sequences conferring the resistance. Linkage disequilibrium indeed is used to describe common inheritance of genomic sequences in a cross population analysis when no linkage exists. Linkage describes common inheritance of genomic sequences in a population structure pending on the frequency of recombination.

The linkage disequilibrium score may be any positive score, meaning that the association of SNP#3 and/or SNP#9 with the introgressed sequences is not random.

In a plant or seed of the invention, thus comprising in its genome introgressed sequences from *Citrullus colocynthis*, said introgressed sequences are preferably to be found in the genome at a genetic distance of less than 20 cM, preferably less than 15 cM, most preferably less than 10 cM, and even preferably less than 5 cM from the locus corresponding to SNP#3.

In another embodiment said introgressed sequences from *Citrullus colocynthis* are preferably to be found in the genome at a genetic distance of less than 20 cM, preferably less than 15 cM, most preferably less than 10 cM, and even preferably less than 5 cM from the locus corresponding to SNP#9.

In a preferred embodiment, the introgressed sequences from *Citrullus colocynthis* are to be found in the genome of a plant or seed of the invention at less than 20 cM from both SNP#3 and SNP#9, or preferably less than 15 cM from both; for example the introgressed sequences are located at less than 5 cM from the locus corresponding to SNP#3 and at 15 cM at most from SNP#9. Alternatively, the introgressed sequences may be located in the genome of a plant or seed of the invention at less than 5 cM from the locus corresponding to SNP#9 and at 15 cM at most from SNP#3. According to a particularly preferred embodiment, the introgressed sequences are located at less than 5 cM from both the locus encompassing SNP#3 and the locus encompassing SNP#9.

According to an embodiment, a seed or plant of the invention is characterized by the presence of allele C of SNP#3 on chromosome 6, in combination with absence of allele T of said SNP. Indeed, presence of allele C of SNP#3 confirms the presence of introgressed sequences from *Citrullus colocynthis* at the locus of SNP#3; moreover the absence of allele T confirms that the introgressed sequences are homozygously present, i.e. present on all the homologues of chromosome 6.

According to another embodiment, a seed or plant of the invention is characterized by the presence of allele C of SNP#9 on chromosome 6, in combination with absence of allele T of said SNP. Indeed, presence of allele C of SNP#9 confirms the presence of introgressed sequences from *Citrullus colocynthis* at the locus of SNP#9; moreover the absence of allele T confirms that the introgressed sequences are homozygously present, i.e. present on all the homologues of chromosome 6.

In a preferred embodiment, in a genome of a plant or seed of the invention, both allele C of SNP#3 and allele C of SNP#9 are present, and the other alleles of these SNP are absent, namely allele T of SNP#3 and allele T of SNP#9 are absent.

In another embodiment, in the genome of a *C. lanatus* plant or seed of the invention, the introgressed sequences are preferably to be found within a chromosomal interval delimited on chromosome 6 by the location of SNP#1 (SEQ ID No:1) on one side and the location of SNP#10 (SEQ ID No:10) on the other side. The introgressed sequences from *Citrullus colocynthis* conferring the resistance are preferably to be found within this chromosomal interval. The introgressed sequences responsible for the resistance may either be found strictly within the interval defined by SNP#1 and SNP#10, meaning that the allele of SNP#1 and the allele of SNP#10 are the alleles representative of *C. lanatus* sequences, or alternatively the introgressed sequences are also encompassing SNP#1 or SNP#10, or both SNP#1 and SNP#10.

According to a preferred embodiment of the present invention, the introgressed sequences or interval from *Citrullus colocynthis* present in the genome of a seed or plant of the invention and conferring the resistance to geminiviruses, are at least 5 kilobases long, and preferably at least 8, 10 or 15 kb long.

Preferably, the introgressed sequences or intervals from *C. colocynthis* are however not too long in order to avoid introgression of non-commercial features associated with the *C. colocynthis* genotype. It is thus preferred according to the invention that the introgressed sequences mentioned above are less than 25 cM in length, preferably less than 20 cM or less than 15 cM. According to more preferred embodiments, the introgressed sequences are less than 10 cM or even less than 5 cM in length and most preferably less than 5 cM in order to avoid or limit linkage drag.

According to a preferred embodiment, said introgressed sequences are minimized to contain as few as possible sequences unrelated to the desired phenotype.

The resistance and/or tolerance according to the invention is a resistance and/or tolerance to geminivirus infection in general. According to a preferred embodiment, the resistance conferred by the introgressed sequences is a resistance to begomoviruses, and more specifically a resistance to Watermelon Chlorotic Stunt Virus (WmCSV) and/or to Squash Leaf Curl Virus (SLCV).

The seed or plant according to this aspect of the invention is preferably highly resistant to geminiviruses, inter alia it remains free of symptoms (namely chlorosis and stunting for WmCSV infection) till the end of the season when grown under natural infection conditions. With respect to the ploidy of the seed or plant of the invention, they may be of any ploidy level, inter alia diploid, triploid, tetraploid or allopolyploid. Preferably, plant or seed of the invention are diploid, triploid or tetraploid, all of which are used for the development of seedless watermelons (see example 8 in this respect). Triploid watermelons are indeed created by crossing a tetraploid (4×) female parent line with diploid (2×) male parent line. The resulting triploid (3×) watermelon seeds or plants are planted in a field with diploid (2×) watermelon pollenizers. The resulting fruit of the triploid watermelon are seedless. The diploid and tetraploid parents need to be both resistant as the resistance according to the invention is of recessive nature, giving rise to a triploid watermelon plant, which is also resistant to geminiviruses, insofar as both parents are homozygously resistant. The present invention concerns all these resistant plants, as well as seeds giving rise to these plants.

Plants or seeds of the invention, resistant to geminiviruses, are also preferably resistant or tolerant to another pest, especially to pest of major agricultural importance. According to a preferred embodiment, plants or seeds of the invention are also resistant to Powdery Mildew caused inter alia by the fungus *Podosphaera xanthii* (syn. *Sphaerotheca fulginea*) or by *Erysiphe cichoracearum*. In this regard, plants or seeds of the invention comprise in their genome sequences conferring resistance to Powdery Mildew. Suitable sequences conferring said resistance are well known to the skilled man (see inter alia Tetteh et al, 2010; Tetteh et al 2013 and Davis et al, 2007). Plants or seeds resistant to both geminiviruses and Powdery Mildew can be obtained by different techniques well known to the person skilled in the domain of the invention. Starting from plants or seeds according to the invention, resistant to geminiviruses, the supplemental resistance to powdery mildew can be added through molecular cloning and genetic modification, or through crossing and selfing of a plant of the invention with a *C. lanatus* plant resistant to powdery mildew.

As detailed above, the invention is directed to *C. lanatus* plants, resistant to geminiviruses infection, as well as to seeds giving rise to those plants.

A *C. lanatus* plant according to the invention may be a commercial plant or line or variety, preferably cultivated for its fruits. Such a commercial plant or line gives rise to fruits, when grown in suitable conditions and when adequately pollenized, which are marketable.

Marketable watermelon fruits are inter alia characterized by a deep red flesh color, preferably a deep red—44A flesh color, and/or a flesh firmness of less than 4 according to the scoring system defined in the present invention, and/or a flesh fiber content of less than 2 according to the scoring system defined above, and/or a fruit taste of at least 3, according to the scoring system defined above. A marketable watermelon fruit is preferably characterized by the presence of all the features mentioned above, i.e. a deep red—44A flesh color, a flesh firmness of less than 4, a flesh fiber content of less than 2 and a fruit taste of at least 3.

A marketable watermelon fruit is also preferably a seedless fruit. Plants or seeds giving rise to seedless fruits are generally triploid.

A preferred seed or plant of the invention is thus capable of bearing watermelon fruits having a red flesh color, preferably a deep red—44A flesh color. Preferably, such fruits have also a flesh firmness of less than 4, a flesh fiber content of less than 2 and a fruit taste of at least 3.

The invention also concerns seeds or plants capable of bearing fruits having a brix level higher than 11 and/or a weight larger than 2.5 kg.

Another plants or seeds according to the invention are also those giving rise to pollenizers, especially lines used for pollenizing triploid plants. Such plants are generally characterized by small size, or multibranching phenotype. The invention also concerns diploid lines which are to be treated for doubling of their chromosome number, as well as resulting tetraploid lines.

A plant or seed according to the invention may be a progeny or offspring of a plant grown from the deposited seeds of *Citrullus lanatus*—WMCSVR, deposited at the NCIMB under the accession number NCIMB 42197. Plants grown from the deposited seeds are indeed homozygously resistant to geminiviruses, they thus bear in their genome the introgressed sequences from *C. colocynthis* conferring resistance and/or tolerance to geminiviruses, on both homologues of chromosome 6. They can be used to transfer these sequences in another background by crossing and selfing and/or backcrossing.

The introgressed sequences from *C. colocynthis* conferring resistance, or tolerance, depending on the conditions, to geminiviruses according to the present invention are homozygoulsy present in the genome of a resistant plant or seed. Accordingly, such a plant exhibits, on both homologues of chromosome 6, introgressed sequences from *C. colocynthis* capable of conferring resistance to geminiviruses when present homozygously. It must be borne in mind that this thus not necessarily implies that the introgression fragments from *C. colocynthis* on both chromosome 6 homologues are identical. Indeed, one of the homologue may comprise only the introgressed sequences necessary and sufficient to confer resistance, whereas the other homologue comprises a larger introgression fragment, comprising said sequences in addition to further sequences from *C. colocynthis* unrelated to resistance.

The invention is also directed to the deposited seeds *Citrullus lanatus*—WMCSVR (NCIMB 42197) and to plants grown from one of these seeds. These seeds contain homozygously the introgressed sequence conferring the phenotype of interest; they are however distinct on other phenotypic traits such that they do not form a plant variety.

The invention is also directed to resistant plants or seeds as defined above, i.e. containing the introgressed sequences of interest in homozygous form, obtainable by transferring the introgressed sequences from a resistant *C. lanatus* plant, representative seeds thereof were deposited under NCIMB accession NCIMB-42197, into another *C. lanatus* genetic background, for example by crossing said resistant plant with a second watermelon plant parent.

In a second aspect, the invention also concerns a second type of plants or seeds, namely plants or seeds of *Citrullus lanatus*, which bear in their genome the introgressed sequences from *C. colocynthis* conferring resistance, and/or tolerance, to geminiviruses when present homozygously, but which do not bear these sequences on every homologues of chromosome 6; i.e. they are heterozygous for the introgressed sequences conferring resistance and/or tolerance, namely heterozygous for the resistance locus, or resistance gene. Namely, if the plant is diploid, one chromosome 6 does not comprise the introgressed sequences of interest; if the plant is triploid, one or two of the chromosomes 6 do not comprise the introgressed sequences of interest, if the plant is tetraploid, one, two or three of the chromosomes 6 do not comprise the introgressed sequences of interest. The introgressed sequences of interest are those as defined previously, a copy of which is present in the genome of the deposited seeds, accession number NCIMB 42197.

Due to the fact that the introgressed sequences are present heterozygously in the second type of plants or seeds of the invention, these plants do not exhibit the phenotype of interest, i.e. they are not resistant or tolerant to geminiviruses, the resistance/tolerance trait segregates further to self-pollinations and the phenotype is not expressed when crossing them with other susceptible plants.

According to the invention, said heterozygous plants can be obtained by crossing one homozygous plant mentioned above with a second plant of the *Citrullus lanatus* species, the second plant being susceptible to geminiviruses and not bearing the introgressed sequences of the invention. For example, a plant according to this embodiment of the invention can be obtained by crossing a plant grown from a seed of *Citrullus lanatus*—WMCSVR, deposited at the NCIMB under the accession number NCIMB 42197, with a geminiviruses-susceptible *Citrullus lanatus* parental line not bearing introgressed sequences from *C. colocynthis*.

This parental line can for example be a male sterile *Citrullus lanatus* inbred line.

The second type of plant according to the invention can of course be obtained by other processes.

By self-pollinating diploid plants of the $2^{nd}$ aspect of the invention, the progeny of such a self-pollination will be at 50% also of this type, i.e. bearing the resistance sequences but not displaying the phenotype of interest, at 25% homozygously resistant to geminiviruses as defined in the first aspect of the invention, and at 25% not resistant and not bearing the resistance sequences from *C. colocynthis*. The ratios are different if the plant or seed according to the $2^{nd}$ aspect is not diploid.

The invention therefore concerns any hybrid plant of *Citrullus lanatus* likely to be obtained by crossing a plant resistant to geminiviruses as disclosed in the present description according to the $1^{st}$ aspect, with a susceptible plant of *Citrullus lanatus*. The hybrid plant can be obtained by crossing either a plant resistant to geminiviruses according to the invention as female parent and a plant susceptible to geminiviruses as male parent, or alternatively by crossing a plant resistant to geminiviruses according to the invention as male parent and a plant susceptible to geminiviruses as female parent.

The presence of the introgressed sequences according to the invention can be revealed by the sequencing of the SNP identified by the inventors, and more specifically by allele C of SNP#3 and/or by allele C of SNP#9, preferably by allele C of SNP#3. The heterozygous status of the genome of a plant, seed or plant part with respect to the introgressed sequences of interest can be brought to light by the simultaneous presence of alleles C and T of SNP#3 and/or by the simultaneous presence of alleles C and T of SNP#9. The presence of the introgressed sequences can also be revealed by genic amplification of sequences in the proximity of the SNPs defined in the present invention, especially SNP#3 and SNP#9 and comparison with the sequence of the respective amplification fragment, obtainable by carrying out the amplification on seeds deposited at the NCIMB under accession number NCIMB 42197, as already mentioned in respect of the $1^{st}$ aspect.

The presence of introgressed sequences of interest can also be characterized by one or more of the following alleles: allele A of SNP#1 (SEQ ID No:1), allele G of SNP#2 (SEQ ID No:2), allele T of SNP#4 (SEQ ID No:4), allele C of SNP#5 (SEQ ID No:5), allele G of SNP#6 (SEQ ID No:6) and allele C of SNP#7 (SEQ ID No:7), as detailed above, in addition or in place of allele C of SNP#3 and/or allele C of SNP#9.

The invention also concerns any plant likely to be obtained from seed or plants of the invention as described above, and also plant parts of such a plant, and most preferably explants, scion, cutting, seed, fruit, rootstock, pollen, ovules and any other plants part, wherein said plant, explants, scion, cutting, seed, fruit, rootstock, pollen, ovules, and/or plant part is obtainable from a seed or plant according to the first embodiment of the invention, i.e. bearing the introgressed sequences of interest homozygously in their genome or from a seed or plant according to the second embodiment of the invention, i.e. bearing the introgressed sequences of interest heterozygously in their genome. These plant parts, inter alia explants, scion, cutting, seed, fruit, rootstock, pollen, ovules, comprise in their genome the introgressed sequences from *C. colocynthis* conferring the resistance to geminiviruses when present homozygously. The introgressed sequences referred to in this aspect of the invention are those defined above in the context of plants of the invention. The different features of the introgressed sequences defined in relation with the first aspect of the invention apply mutatis mutandis to this aspect of the invention. The introgressed sequences are thus preferably chosen from those present in the genome of a plant corresponding to the deposited material *Citrullus lanatus*—WMCSVR (NCIMB accession number 42197). They are advantageously characterized by the presence of allele C for SNP#3 and/or allele C for SNP#9; preferably by allele C of SNP#3.

The invention is also directed to cells of *Citrullus lanatus* plants, such that these cells comprise, in their genome, introgressed sequences from *C. colocynthis* conferring the phenotype of interest, i.e. resistance and/or tolerance to geminiviruses when present homozygously. The introgressed sequences are those already defined in the frame of the present invention, they are characterized by the same features and preferred embodiments already disclosed with respect to the plants and seeds according to the preceding embodiments of the invention. The presence of these introgressed sequences can be revealed by the techniques disclosed above and well known to the skilled reader. It can inter alia be determined whether the introgressed sequences are present homozygously or heterozygously in the genome of such a cell of the invention. They are advantageously characterized by the presence of allele C for SNP#3 and/or allele C for SNP#9, preferably by allele C of SNP#3. Cells according to the invention can be any type of the *Citrullus lanatus* cell, inter alia a cell capable of regenerating a whole *Citrullus lanatus* plant, bearing the introgressed sequences from *C. colocynthis*.

The present invention is also directed to a tissue culture of regenerable cells of the plant as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls, and contain in their genome introgressed sequences from *C. colocynthis* on chromosome 6 conferring resistance and/or tolerance to geminiviruses only when present homozygously.

The tissue culture will preferably be capable of regenerating plants having the physiological and morphological characteristics of the foregoing watermelon plant, and of regenerating plants having substantially the same genotype as the foregoing watermelon plant. The present invention also provides watermelon plants regenerated from the tissue cultures of the invention.

The invention also provides a protoplast of the plant defined above, or from the tissue culture defined above, said protoplast containing said introgressed sequences from *C. colocynthis* conferring resistance to geminiviruses when present homozygously.

According to a fourth aspect, the present invention is also directed to the use of a watermelon plant as detailed according to the first aspect of the invention, i.e. resistant, or tolerance depending on the infection conditions, to geminiviruses, especially to begomoviruses, as a breeding partner in a breeding program for obtaining *C. lanatus* plants resistant and/or tolerant to geminiviruses. Indeed, such a watermelon plant according to the first aspect harbors homozygously in its genome introgressed sequences from *C. colocynthis*, conferring the phenotype of interest, i.e. resistance and/or tolerance. By crossing this plant with susceptible or less resistant plants, it is thus possible to transfer these sequences, conferring the desired phenotype, to the progeny as the phenotype is a monogenic trait. A plant according to the invention can thus be used as a breeding partner for introgressing sequences conferring the desired phenotype into a *C. lanatus* plant or germplasm. Although a plant or seed according to the second aspect of the invention, i.e. bearing the introgressed sequences of interest heterozygously, can also be used as a breeding partner as detailed above, the segregation of the phenotype is likely to render the breeding program more complex.

The introgressed sequences from *C. colocynthis* will advantageously be introduced into varieties that contain other desirable genetic traits such as resistance to disease, early fruit maturation, drought tolerance, fruit shape, seedlessness, and the like.

The invention is also directed to the same use with plants or seed of *Citrullus lanatus*—WMCSVR, deposited at the NCIMB under the accession number NCIMB 42197. Said plants are also suitable as introgression partners in a breeding program aiming at conferring the desired phenotype to a *C. lanatus* plant or germplasm.

In such a breeding program, the selection of the progeny displaying the desired phenotype, or bearing sequences linked to the desired phenotype, can advantageously be carried out on the basis of the alleles of the SNP markers. The progeny is preferably selected on the presence of allele C of SNP#3 or allele C of SNP#9 on chromosome 6, preferably of allele C of SNP#3. The selection can alternatively be made on the basis of the simultaneous presence of allele C of SNP#3 and allele C of SNP#9.

Alternatively, the other SNPs of the invention, namely SNP#1, SNP#2, SNP#4, SNP#5, SNP#6 and SNP#7 can also be used as detailed above.

The present inventors have indeed confirmed in enclosed example 9, that allele C of SNP#3 allows a genetic selection of resistant plant in a breeding program with a predictability of more than 98%.

The selection of the progeny having the desired phenotype can also be made on conditions of geminiviruses infection, as disclosed inter alia in example 1 for WmCSV infection and in example 7 for SLCV infection.

A plant according to the invention, or grown from a seed as deposited under accession number NCIMB 42197, is thus particularly valuable in a marker assisted selection for obtaining commercial watermelon lines and varieties resistant to geminiviruses infection, especially to begomoviruses such a WmCSV and SLCV.

The invention is also directed to the use of said plants in a program aiming at identifying, sequencing and/or cloning the genes conferring the desired phenotype, i.e. resistance to geminiviruses, especially to begomoviruses such a WmCSV and SLCV.

Any specific embodiment described for the $1^{st}$, $2^{nd}$ and $3^{rd}$ aspects of the invention is also applicable to this aspect of the invention, especially with regard to the features of the introgressed sequences from *C. colocynthis* conferring the resistance when present homozygously.

According to a fifth aspect, the invention also concerns methods or processes for the production of *C. lanatus* plants having the desired phenotype, especially commercial plants. Preferably such plants are also resistant to Powdery Mildew caused inter alia by the fungus *Sphaerotheca fulginea* or by *Erysiphe cichoracearum*.

The present invention is indeed also directed to transferring the introgressed sequences conferring the resistance and/or tolerance, in the watermelon plant to other watermelon varieties and species and is useful for producing new types and varieties of geminivirus resistant or tolerant watermelon.

A method or process for the production of a plant having these features may comprise the following steps:
  a) Crossing a plant corresponding to the deposited seeds (NCIMB 42197) and a susceptible or less resistant *C. lanatus* plant, in which the desired phenotype is to be imported or improved.
  b) Selecting a plant in the progeny thus obtained bearing sequences conferring resistance to geminiviruses only when present homozygously,
  c) Self-pollinating one or several times the plant obtained at step b) and selecting a resistant plant in the progeny thus obtained;
wherein SNPs markers are used in steps b) and c), for selecting plants bearing sequences conferring resistance to geminiviruses only when present homozygously and/or plants resistant to geminiviruses. The SNP markers are preferably one or more of the 9 SNP markers of the invention, and preferably SNP#3 and/or SNP#9, most preferably SNP#3. According to a preferred embodiment, the selection is at least partly made on the basis of the allele of SNP#3 and/or SNP#9 on chromosome 6. The selection is preferably carried out by detecting the alleles of these 2 SNP markers. Alternatively, the selection can be made on the detection of the allele of at least 2 SNPs chosen amongst SNP#1, SNP#2, SNP#3, SNP#4, SNP#5, SNP#6, SNP#7 and SNP#9, preferably at least 3 SNPs, for example at least 4, 5 or 6, one of them being either SNP#3 or SNP#9. The selection can also be made on the detection of the alleles of all these 8 SNPs.

The plant, which is selected at the selection step disclosed above, is preferably selected on the presence of allele C of SNP#3 and/or of allele C of SNP#9, preferably by allele C of SNP#3. In order to identify plants bearing homozygously the introgressed sequences responsible for the resistance to geminiviruses, the presence of allele C of SNP#3 is detected in combination with the absence of allele T of SNP#3;

and/or the presence of allele C of SNP#9 is detected in combination with the absence of allele T of SNP#9.

Preferably, the susceptible or less resistant *C. lanatus* plant of step a) is resistant to Powdery Mildew. This plant is preferably an elite line, used in order to introduce commercially desired traits or desired horticultural traits.

A method or process for the production of a plant having these features may also comprise the following additional steps:

d) Backcrossing the resistant plant selected in step c) with a susceptible *C. lanatus* plant (i.e. susceptible to geminivirus infection);
e) Selecting a plant in the progeny bearing sequences conferring resistance to geminiviruses only when present homozygously,
f) Self-pollinating the plant obtained at step e) or crossing distinct plants obtained at step e), and
g) Selecting a plant resistant to geminiviruses.

According to a preferred embodiment, the susceptible *C. lanatus* plant of step d) is also resistant to Powdery Mildew.

A plant corresponding to the deposited seeds can be either a plant grown from the deposited seeds or any plant according to the 1st aspect of the invention, i.e. homozygously resistant to geminiviruses.

Alternatively, the method or process may comprise the following steps:

a1) Crossing a plant corresponding to the deposited seeds (NCIMB 42197) and a susceptible or less resistant *C. lanatus* plant, in which the desired phenotype is to be imported or improved, thus generating the F1 population.
a2) Advancing the F1 population to create F2 population;
b) Selecting resistant individuals in the progeny thus obtained;
c) Optionally self-pollinating one or several times the resistant plant obtained at step b) and selecting a resistant plant in the progeny thus obtained;
d) Optionally backcrossing the resistant plant selected in step b) or c) with a susceptible *C. lanatus* plant (i.e. susceptible to geminivirus infection),
e) Selecting in the progeny a plant bearing sequences linked to the desired phenotype,
f) Self-pollinating the plant obtained at step e) or crossing distinct plants obtained at step e), one or several times, and
g) selecting a plant resistant to geminiviruses.

The plant selected at step b), c) or g) of the preceding methods may be a commercial plant, especially a plant having fruits which have a deep red—44A flesh color, a flesh firmness of less than 4, a flesh fiber content of less than 2 and/or a fruit taste of at least 3, at full maturity in normal culture conditions.

Steps d), e) and/or f) may be repeated twice or three times or more, not necessarily with the same susceptible *C. lanatus* plant. Said susceptible *C. lanatus* plant is preferably a breeding line. According to a preferred embodiment, the susceptible *C. lanatus* plant of step d) is also resistant to Powdery Mildew. This plant is preferably an elite line, used in order to introduce commercially desired traits or desired horticultural traits.

The self-pollination/crossing and backcrossing steps may be carried out in any order and can be intercalated, for example a backcross can be carried out before and after one or several self-pollinations/crossings, and self-pollinations/crossings can be envisaged before and after one or several backcrosses.

Moreover, the methods of the invention are advantageously carried out by using SNP markers for one or more of the selection steps for selecting plants bearing the introgressed sequences linked to the geminivirus resistance and/or tolerance, or for selecting plants having the phenotype of interest.

The SNP markers are preferably one or more of the 8 SNP markers of the invention, and preferably SNP#3 and/or SNP#9, most preferably SNP#3. According to a preferred embodiment, the selection is at least partly made on the basis of the allele of SNP#3 and/or of SNP#9 on chromosome 6. The selection is preferably carried out by detecting the alleles carrying/characterized by these 2 SNPs.

The plant selected at the selection step disclosed above is preferably selected on the presence of allele C of SNP#3 and/or allele C of SNP#9, preferably allele C of SNP#3. In order to identify plants bearing homozygously the introgressed sequences responsible for the resistance to geminiviruses, the presence of allele C of SNP#3 is detected in combination with the absence of allele T of SNP#3; and/or the presence of allele C of SNP#9 is detected in combination with the absence of allele T of SNP#9.

Alternatively, the other SNPs of the invention can also advantageously be used, namely SNP#1, SNP#2, SNP#4, SNP#5, SNP#6 and SNP#7, preferably SNP#2, SNP#4, SNP#5 and SNP#6, in place or advantageously in addition to SNP#3 and SNP#9.

The selection of the progeny having the desired phenotype can also be made on conditions of geminivirus infection, as disclosed inter alia in example 1 for WmCSV or in example 7 for SLCV.

The method used for allele detection can be based on any technique allowing the distinction between two different alleles of a SNP, on a specific chromosome locus.

The invention is also directed to a method or process for obtaining *C. lanatus* plants having the desired phenotype, wherein said method comprises the steps of:

a) Making an interspecific cross between a *C. colocynthis* plant resistant to geminiviruses and a susceptible *C. lanatus* plant,
b) Selecting one plant bearing sequences linked to the desired phenotype,
c) Self-pollinating one or several times the resistant plant obtained at step b) and selecting a resistant hybrid in the progeny thus obtained;
d) Backcrossing the resistant hybrid selected in step c) with a susceptible *C. lanatus* plant (i.e. susceptible to geminivirus infection);
e) Selecting a plant bearing sequences linked to the desired phenotype,
f) Self-pollinating the plant obtained at step e), and
g) Selecting a plant resistant to geminivirus infection, wherein steps d) to g) can be repeated and wherein SNPs markers are used in steps b), c), e) and/or g) for selecting plants resistant to geminiviruses or bearing sequences linked to the desired phenotype when present homozygously, as detailed for the previous methods.

The plant selected at step g) may be a commercial plant, especially a plant having fruits which have a deep red—44A flesh color, a flesh firmness of less than 4, a flesh fiber content of less than 2 and/or a fruit taste of at least 3, at full maturity in normal culture conditions.

The invention also concerns a method wherein steps a) to c) are not carried out and wherein step d) is carried out with a plant obtained from the deposited seed (NCIMB accession number 42197) instead of the resistant hybrid mentioned above in step d).

All preferred embodiments recited above for the previous method apply mutatis mutandis to this alternative method. Especially, steps d) and e) can be repeated, they are preferably carried out twice, or three times. The same applies to steps f) and g) which are preferably carried out twice, three times or more.

The present invention also concerns any breeding scheme involving as first step crossing a plant grown from one of the deposited seeds (NCIMB 42197). The invention thus is directed inter alia to the following breeding scheme:

(i.) sowing seeds of the deposited seeds (NCIMB 42197), and selecting plants bearing desired horticultural traits, such as red flesh color, brix level (higher than 11) and/or weight larger than 2.5 kg;

(ii.) crossing the selected plants with a *C. lanatus* line, resistant to Powdery Mildew. Such a line can be for example PI189225 (see Tetteh et al, 2010), which is a well-known accession, enriched with negative horticultural traits such as bitterness, white fibrous low brix flesh, flattened fruit shape;

(iii.) Selfing the F1 obtained at step (ii) to obtain an F2 population, (iv.) Selecting plants homozygously resistant to geminiviruses, especially to WmCSV, and also resistant to Powdery Mildew, and selfing to obtain F3 plants;

(v.) Phenotyping the F3 plants for Powdery Mildew resistance, selecting plants resistant to both geminiviruses and Powdery Mildew and crossing them with an elite line in order to introduce commercially desired traits;

(vi.) Selfing the F1 plants obtained at the end of step (v.) thus obtaining F2 plants;

(vii.) Selecting plants homozygously resistant to geminiviruses, especially to WmCSV, and also resistant to Powdery Mildew and crossing them with an elite line in order to introduce commercially desired traits;

(viii.) Selfing the BC1F1 plants obtained at the end of step (vii.) thus obtaining BC1F2 plants;

(ix.) Selecting plants homozygously resistant to geminiviruses, especially to WmCSV, and also resistant to Powdery Mildew and crossing them with an elite line in order to introduce commercially desired traits;

(x.) Selfing the BC2F1 plants obtained at the end of step (ix.) thus obtaining BC2F2 plants;

(xi.) Selecting plants homozygously resistant to geminiviruses, especially to WmCSV, also resistant to Powdery Mildew and also having the commercially desired traits and selfing them one or several times (BC2F3 to for example BC2F10), in order to fix the traits and obtain uniform lines.

In order to obtain commercial hybrid plants (2n), homozygously resistant to geminiviruses, especially to WmCSV, resistant to Powdery Mildew and with commercially desired traits, the lines obtained at the end of step (xi.) can be crossed two by two.

In order to obtain triploid watermelon plants, the following steps are carried out:

(xii.) Treating plants with chromosome doubling agent, for example colchicine, thus obtaining plants T1 (4n);

(xiii.) Crossing these plants with a line (2n) resistant to Powdery Mildew and resistant to geminiviruses, homozygous for the sequences conferring the resistance (for example a line obtained at the end of step xi.), and having the desired commercial traits;

(xiv.) Obtaining an hybrid F1 (3n) resistant to Powdery Mildew and resistant to geminiviruses, namely homozygous for the sequences conferring the resistance, and with the desired commercial traits.

In order to obtain commercial hybrid plants (2n), homozygously resistant to geminiviruses, especially to WmCSV, and with commercially desired traits, the above described scheme is modified according to the following: at step ii.) above, crossing is carried out with a *C. lanatus* line instead of a *C. lanatus* line, resistant to Powdery Mildew; giving rise to F1 plants which are selfed (F2 plants), selected for resistance to geminiviruses and desired commercial traits; the plants thus obtained are selfed one or several times, in order to fix the traits and obtain uniform lines, which are then crosses two by two for obtaining commercial hybrids (2n) resistant to geminiviruses.

In all the methods described above, although the phenotype of interest is mainly referred to as resistance, the invention also concerns tolerance to geminiviruses.

The present invention also concerns a plant obtained or obtainable by one of the methods described above. Such a plant is indeed a *C. lanatus* plant having the desired phenotype according to the first aspect of the invention, i.e. resistant and/or tolerant to geminiviruses, especially begomoviruses including WmCSV, such a plant is also advantageously resistant to Powdery Mildew. Depending on the number of steps carried out, such a plant is diploid, triploid (see inter alia step xiv. above) or tetraploid (see inter alia step xii. above).

The invention also provides a method for producing a hybrid *Citrullus lanatus* seed comprising crossing a first cultivar plant parent with a second cultivar plant parent and harvesting the resultant hybrid *Citrullus lanatus* seed, wherein both parents are cultivars containing the introgressed sequences in the homozygous state. The hybrid seeds, plant and parts thereof produced by such method are also part of the invention.

The invention is moreover directed to a method for detecting and/or selecting *C. lanatus* plants having introgressed sequences from *C. colocynthis* conferring resistance and/or tolerance to geminiviruses when present homozygously, on the basis of the allele detection of at least one SNP chosen amongst SNP#3 and SNP#9 on chromosome 6, preferably SNP#3. The method is preferably to be carried out on *C. lanatus* plants resistant/tolerant to geminiviruses, especially on plants resistant or tolerant to WmCSV; the method thus can be used to confirm that such plants comprise in their genome the introgressed sequences from *C. colocynthis* according to this invention, and thus have been obtained according to the present invention. Preferably, plants bearing the introgressed sequences are selected if at least one of the following markers is detected: allele C of SNP#3 and allele C of SNP#9, in a genetic material sample of the plant to be selected. According to a preferred embodiment, the allele of interest which is detected is present homozygously in the selected plant, i.e. no other allele of said SNP is present. In such a case, it can be concluded that the plant bears the introgressed sequences and is resistant to geminiviruses.

According to a particularly preferred embodiment, the selection is thus made on the simultaneous presence of allele C of SNP#3 and allele C of SNP#9. For selection of plants displaying the phenotype of resistance and/or tolerance to geminiviruses, the selection is preferably made on the simultaneous detection of allele C of SNP#3 and allele C of SNP#9 in combination with no detection of any other allele for these SNPs, and especially no detection of allele T of SNP#3 or allele T of SNP#9.

Such a combination of alleles is to be found in plants grown up from to the deposited seeds. The detection or selection may also comprise the identification of the alleles at least one of SNP#4, SNP#5, SNP#6, and SNP#7, or at least 2, 3, or all 4 SNPs, or the identification of the alleles of at least one of SNP#1, SNP#2, SNP#4, SNP#5, SNP#6 and SNP#7, preferably SNP#2, SNP#4, SNP#5 and SNP#6, in addition to SNP#3 or SNP#9, or in addition to both SNP#3 and SNP #9.

In addition to introgression of the sequences conferring resistance (or tolerance, depending on the infection conditions) to geminiviruses infections, as detailed in the methods of the invention, these sequences of the invention can also be introduced into C. lanatus background by genetic engineering in order to obtain a commercial C. lanatus plant resistant to geminiviruses. The identification and cloning of the introgressed sequences from C. colocynthis conferring the desired phenotype, inter alia from the deposit NCIMB 42197, can be carried out by the skilled person, on the basis of the sequence information given in the present application and deposited material.

According to a further aspect, the present invention is also directed to hybrid plants of C. lanatus, obtainable by crossing a resistant plant according to the first aspect of the invention, or a resistant plant obtainable by the methods disclosed above, with a plant of C. lanatus, for example a plant susceptible to geminiviruses infection, or a plant with a different level of resistance to geminiviruses infection.

A particularly preferred hybrid C. lanatus plant, is a plant which displays male sterility, or any other trait or phenotype of agronomical interest.

EXAMPLES

Example 1: WmCSV Inoculation and Disease Screening

Watermelon chlorotic stunt virus (WmCSV) is caused by a whitefly transmitted geminivirus. The identification of source of resistance involves the development of a phenotyping system based on the four following aspects that have to be validated for repeatability and reliability:
the virus growth and maintenance,
the vector growth and maintenance,
the inoculation
and the scoring methodologies.

Virus Growth and Maintenance

The Watermelon chlorotic stunt virus (WmCSV) was maintained on isolated infected watermelon plants (Citrullus lanatus) grown in an insect-proof greenhouse. Cultures of the WmCSV were maintained on susceptible watermelon plants (Citrullus lanatus) 'Malali' (Hazera Genetics Ltd, now Hazera Seeds Ltd).

Whitefly Maintenance

Whitefly (Bemisia tabaci, biotype B) colonies were reared on cotton (Gossypium hirsutum L.) plants grown in muslin-covered cages maintained inside an insect-proof greenhouse with natural lighting and temperature control (30° C. during the day and 25° C. during the night). Adult whiteflies were provided with a 48-h acquisition access period on WmCSV infected watermelon plants (Citrullus lanatus) 'Malali'.

Inoculation of Plants

The acquisition access period was followed by a 48-h inoculation access period on the watermelon (Citrullus lanatus) plants to be tested for resistance to WmCSV, said plants being at the two true leaves development level. Following the inoculation access period, the whiteflies were removed by treating plants with imidacloprid (Confidor; Bayer, Leverkusen, Germany). The plants were kept in the greenhouse (insect-proof greenhouse with natural lighting and temperature control (30° C. during the day and 25° C. during the night), during spring and late summer/fall seasons (April and August, respectively), for a four weeks incubation period.

Disease Screening

The development of symptoms (leaves in upper part of plant yellowing and internodes shortening) was followed and registered 30 days post inoculation (DPI) using two levels, namely resistant or susceptible, on individual plant basis. Susceptible plants were discarded and resistant plants were transplanted in a plastic tunnel for a second symptoms evaluation 60 days post inoculation (DPI) on grown plants, using the same levels as the first screen (resistant or susceptible). A plant was considered as resistant only if it had no WmCSV symptoms at 30 and 60 DPI.

Example 2: Test of a Possible Source of Resistance to Watermelon Chlorotic Stunt Virus (WmCSV)

As a starting point of the realization of the invention, the present inventors have identified a Citrullus colocynthis as a possible source of resistance to Watermelon Chlorotic Stunt Virus (WmCSV). A Citrullus colocynthis (COLO1) was collected by the inventors in the 90' in the south part of the Israeli Negev desert. This plant, which fruits are bitter, have firm and fibrous flesh as well as very low sugar content, was crossed with a Citrullus lanatus (LANA1) plant and the resulting hybrid was selfed and backcrossed two times. The BC2F2 plant population (33 plants) was surprisingly found segregating for the WmCSV resistance (26 susceptible for 7 resistant plants). All the resistant plants fruits had a very pour flesh quality, with a light pink flesh color and firm and fibrous flesh, all characteristics that would render any watermelon fruit unmarketable. The inventors had to find ways to get rid of these unwanted phenotypic characteristics. The BC2F2 plants were once more backcrossed to the original Citrullus lanatus watermelon plant, which progeny again showed a segregating population of 60 susceptible plants for 20 resistant once. It was then considered that the resistance was due to a single recessive gene. The BC3F2 resistant plants were self-pollinated and one BC3F3 plant, when self-pollinated, showed a stabilization for the resistance. This BC3F3 plant harbored two copies of the recessive resistance gene. More surprisingly, while the other BC3F3 plants still had poor flesh colors, the one having the two copies of the recessive resistance gene also has a red flesh color. The plant was further self-pollinated for two other generations, up to a BC3F6 plant that showed resistance to WmCSV, a red flesh as well as tiger rind color (distinctive stripes on lighter rind color, which can easily be identified). In addition, the fruits also had a flesh brix higher than 12 without any fibers.

| Characteristic* | Citrullus colocynthis COLO1 | Citrullus lanatus parental material LANA1 | BC3F6 plants |
|---|---|---|---|
| Flesh taste | Bitter | Sweet | Sweet |
| Flesh firmness | Firm | Crisp | Crisp |
| Flesh fibers | Fibrous | No fibers | No fibers |
| Flesh color | White RHS 37B | Deep red RHS 44A | Deep Red RHS 44A |
| Flesh Brix | 5 | >12 | >12 |
| WmCSV resistance | Resistant | Susceptible | Resistant |

Example 3: Addition of Powdery Mildew Resistance

Powdery mildew can decrease plant canopy, limiting yield and increasing the need for fungicide application.

Symptoms of Powdery Mildew on watermelons, useful for the detection, are the following: chlorotic spots that occur on leaves accompanied by little or no sporulation, and only a small amount of mycelial development, or mycelial and conidial development on either leaf surface, with or without the associated chlorotic spots (Davis et al, 2007). The resistance is evaluated in natural inoculated environments.

The BC3F6 plant of example 2 was further crossed with another *Citrullus lanatus* watermelon plant which is resistant to Powdery Mildew. The resulting plants were self-pollinated over three generations where one family was found to be stabilized for WmSCV resistance. Powdery Mildew resistance was assessed with inoculation of *Podosphaera xanthii* race 1 as a dust spray of spores cultivated on susceptible watermelon pants. The inoculated seedlings are incubated first in a growth chamber (temperature range from 23 to 26° C. with humidity) and second, one week after inoculation, in a colder contained (17° C.). Symptoms and sporulations are usually visible after 1 week and scored 2-3 weeks after inoculation, where there are clean differences between resistant and susceptible plants. The plants are scored on a 1 to 4 scale, where 1 are susceptible plants with severe symptoms and sporulations, 2 are plants showing moderate symptoms (in addition to sporulation on hypocotyls, one can see some yellowing and beginning of sporulation on cotyledons), 3 are plants with minor symptoms (no signs of Powdery Mildew on cotyledons and true leaves but still some sporulation on hypocotyls) and 4 are healthy plants, without any signs of powdery mildew.

One plant of the F3 family was scored as 2. This plant was further selfed for three generations, up to F6 level. The plants were again further tested for Powdery mildew resistance and all 27 tested plants were scored 3 showing that in addition to a WmCSV resistance the plants were also resistant to Powdery Mildew.

Example 4: Development of Genetic Data and Molecular Markers

In order to create a mapping population, a resistance source line, obtained from an initial cross with the original *Citrullus colocynthis* COLO1, was crossed with a susceptible elite line LANA1, to produce an F2 population. DNA was isolated from 175 F2 plants that were selfed to produce F3 families. These F3 families were screened for WmCSV resistance (33 plants per family). Disease evaluation was conducted according to the description in example 1, namely the plants were scored resistant or susceptible. Only families of which all 33 plants were found to be resistant were scored as resistant. A bulk of these F3 families were used for the seed deposit NCIMB 42197: this bulk corresponds to a population and is thus not a plant variety. Only families of which all 33 plants showed symptoms, were scored as susceptible. Other families that segregated in the resistance phenotype were scored as segregating.

The genotyping part was done on DNA samples isolated from F2 plants on bulks of resistant samples vs. susceptible samples. In addition, genotyping was done also on two F1 plants and on the source of resistance (COLO1). Each bulk contained DNA samples of 5 individual plants that were scored as resistant or susceptible to WmCSV.

In summary, the genotyping trial included eight samples:
a. Three resistant bulks (5 plants each)
b. Two susceptible bulks (5 plants each)
c. Two F1 samples (individual plants)
d. One sample from the *Citrullus colocynthis* resistance source (COLO1).

Each sample was genotyped on a separate array; in total the experiment included eight arrays.

Array design: Samples were screened on an Agilent SurePrint G3 or High-Definition Custom array 400K (single color) with a total of 82,726 SNPs. Details of the array can be found at manufacture website—http://www.agilent.com.

SNP Discovery Process:

The SNPs that were used for genotyping resulted from alignment between resequencing data of three watermelon lines, including "Black Diamond" and "Charleston Grey" varieties. The probes were designed in variable length, ranging between 21 to 31 bp depending on their GC content, specifically, probe having SEQ ID No:14 for SNP#1, probe having SEQ ID No:15 for SNP#2, probe having SEQ ID No:16 for SNP#3, probe having SEQ ID No:17 for SNP#4, probe having SEQ ID No:18 for SNP#5, probe having SEQ ID No:19 for SNP#6, probe having SEQ ID No:20 for SNP#7, probe having SEQ ID No:21 for SNP#9, probe having SEQ ID No:22 for SNP#10, probe having SEQ ID No:23 for SNP#11, probe having SEQ ID No:24 for SNP#12, probe having SEQ ID No:25 for SNP#13 and probe having SEQ ID No:26 for SNP#14.

All SNPs were represented by four probes, two probes representing the actual SNP and two probes with the additional two possible nucleotides, these probes are used later in the analysis in order to detect the background noise.

SNPs that appeared between more than two pairs of lines in the SNP discovery process, were represented by eight probes on the Chip (four probes in the sense and four in the anti-sense orientation). In this array, a total of 21,876 SNPs met this criterion.

DNA extraction and array hybridization: DNA was extracted from young leaves using QIAGEN DNeasy 96 Plant Kit (www.qiagen.com). Bulks of DNA were prepared by mixing equal amounts of DNA according to WmCSV resistance score. Hybridization was performed at 'Genotypic' India (www.genotypic.co.in), according to the following protocol.

1/Labeling and Hybridization Protocol
a) Restriction Digestion

The DNA quality control test was performed using Nano-drop-1000 (JH Bio, USA) and an agarose gel to determine the quality, purity and quantity. The labeling of DNA samples were carried out with Agilent SureTag DNA labeling kit Lot No (5190-3400) 1.2 µg of genomic DNA was taken in a total of 20.2 µl volume and 5.8 µl of digestion master mix was added to it to obtain the fragments ranging between 200 bp to 500 bp. The samples were incubated at 37° C. for 2 hours followed by heat inactivation of enzymes at 65° C. for 20 minutes.

b) Sample Labeling

5 µl of Random primer mix was added to each of 26 µl of digested sample. The DNA was denatured at 95° C. for 3 minutes followed by snap chill at 40° C. for 5 minutes. 19 µl of labeling master mix containing Cy3-dUTP, dNTP, Buffer and Klenow, was added to the denatured DNA sample and incubated at 37° C. for 2 hours followed by enzyme heat inactivation at 65° C. for 10 minutes.

c) Labeled DNA Cleanup

The labeled samples were cleaned up using Amicon ultra 30 kDa filter size exclusion filter.

d) Hybridization and Wash

4 µg of Cy3-dUTP labeled sample was combined with salmon sperm DNA, Blocking agent and hybridization buffer. The total hybridization volume was 260 µl. The labeled samples in the above hybridization mix were denatured at 95° C. for 3 minutes and incubated at 37° C. for 30 minutes.

The samples were pipetted onto the gasket slide and hybridized onto array (AMADID 44579). The hybridization was carried out at 60° C. for 40 hours in the surehyb chambers (Agilent Technologies). After hybridization, the slides were washed using aCGH Wash Buffer1 (Agilent Technologies, Part Number 5188-5221) at room temperature for 5 minutes and aCGH Wash Buffer 2 (Agilent Technologies, Part Number 5188-5222) at 37° C. for 1 minute. The slides were then washed with Acetonitrile for 10 seconds. The microarray slide was scanned using Agilent Scanner (Agilent Technologies, Part Number G2565CA).

e) Genotyping Analysis and WmCSV Mapping

Analysis was done using the R-package LIMMA (Smyth, 2004), for within array normalization the 'lowess' method was applied (Yang et al., 2002), and for between array normalization the 'quantile' method (Yang and Thorne, 2003). Bulk comparison was done using two tails T-test analysis.

Results

On the basis of watermelon genome published on http://www.icugi.org/cgi-bin/ICuGI/index.cgi, results indicated only one locus on chromosome 6 delimited by SNP#1 located at 880755 bp and SNP#9 located at 3,971,281 bp, had different genotypes between the bulks as shown in table 2.

Physical position on the genome is based on the Version1 of the genome sequence published by the International Watermelon Genomics Initiative (IWGI)—http://www.icugi.org and is susceptible of modifications. The respective positions of the SNP on chromosome 6 are indeed susceptible to inversions or modifications. The present results however clearly indicate that the resistance phenotype is transmitted with the sequences of SNP#1 and SNP#9 such that the sequences conferring the resistance are in linkage disequilibrium with the SNP#1 and SNP#9.

In addition, all F1 plants demonstrated constitutive susceptible performance to WmCSV, confirming the recessive mode of inheritance of the resistance.

TABLE 2

SNPs linked to WmCSV resistance, location and flanking sequences:
Loc: Location on chromosome 6-Nt R: Nucleotide in resistant bulk
Nt S: Nucleotide in susceptible bulk.

| SNP no | Loc. | Nt R | Nt S | sequence |
|---|---|---|---|---|
| #1 | 880 855 | A | C | TTCACACCAAATCCATCCTCATCTTAGCAAAACATCAT AGGCACCAATTTTGTTTGAAGTTAAAATACCATTTTCA TCCATGTAGGATTCATTCAAATTT[A/C]GTCACAAAAC TCTCAAACGTACAATTTTAGTCATGTTCTTTCCTAAATT TCAAAAGTAGTCCTTTTTGGTTAGTTTGAGGTTAATAT TTTTTTATATTAA (SEQ ID No: 1) |
| #2 | 1 611 911 | G | C | AAACTGGCTTCACTATCATCGTCCACCACTAATTGTG GAATTTTCAGCACCCCTTTTTTGGAGTCAAAACTCAC GTCAGTAAGGCTCTTTGTGCCGCTTT[C/G]CTGGAAAT CTATCCCCGCGTCACGAAGCTGTGTTGCATGTCGAAT CACTTGATATTCTGGCCCGGATTTCTTCGTTTTTCTCT CCATACTACCATCCTTA (SEQ ID No: 2) |
| #3 | 2 250 215 | C | T | TGATTCTGTTTGTTTTGCTAACTCCAGGACTTCTCTTT CAGCTTCCCGGAAATCGCAGGTGCTTAGAGTTTGGC AACTTTCACACGAGTGCTGCTTCTAT[C/T]ATCGTCCA TTCGATTCTCTACTTCGGTCTCATTTGCGTCTTCTTAC TCGCCATCAAGGTTCATCTCTACATCGGTTCCTAATAT GACTTGCTCCGATGCC (SEQ ID No: 3) |
| #4 | 3 914 695 | T | C | TCTTCTTCTGGCTATGTATCTGTTGGTGTTAATACTTA TCTTGAGCCCAATGTAGTTTTGGACGACTGCCTTGTT CTTAACCTTCCGGACTTCTATTTCT[T/C]ATATACTGTA TGAATGGTTATCTGTTAAATTTGTCAGTATGATATGAT TTTGACATGACATGTTTTGGCTCTTTCCACTTCTCGTT TTTCTTGGCTACAT (SEQ ID No: 4) |
| #5 | 3 924 533 | C | G | TGATATAGAATGATATTACGATGCAATATAAGTTAAGA GAACATATAAGATTCGTTTGTTTTATATTTCACAATTAC CCCTTTAAATGAAGGCACAAACT[C/G]CCTGAAAGCA CATGAGTCATTTAGTTTAACTTGCGCAGGTACACAATT TGTGTTTTTCCAAGAAAAGGGGTTGGCCTCTTGTGAT AGGGTAAATACTTCG (SEQ ID No: 5) |
| #6 | 3 925 779 | G | C | AATAGGATGTGGCCAAGAGATTCCCCTGCCTTGTTAC ACAATGGACAAACGGTGGCATGAGAGACTGAGATGG AAGTTCTTTCCGGTTGTCAGCTAAATT[G/C]AGGTTCA CGATTCACACCAAAATATTTGTTTTCTTAGGGCTCTTG GTTTTCCAAATTGCATTAAAGATGCTGCAGACCAGATT GGAAAAAGCAGCAAATG (SEQ ID No: 6) |
| #7 | 3 928 953 | C | T | CCTTATGGCTTCTATGCCTGATATACATCAAGCTGTA GAGTTTTTAAGTACCACAATTGTGGGGATAGGGATTG AACTTCCCACCTCAAGGATAGAAGGT[C/T]GTGCCAAT CACCACTGAGCTTACCTCGATTTGGCCATCAAGCTGT AGAGTTGCTCACGCAAGAAAAGGGGAAAACCAGCAC TGCCAATGTCCAAAAACAG (SEQ ID No: 7) |

TABLE 2-continued

SNPs linked to WmCSV resistance, location and flanking sequences:
Loc: Location on chromosome 6-Nt R: Nucleotide in resistant bulk
Nt S: Nucleotide in susceptible bulk.

| SNP no | Loc. | Nt R | Nt S | sequence |
|---|---|---|---|---|
| #9 | 3 971 181 | C | T | GGTGAGGATGGGATTGTTTACGCAATATGTGAACTTC AGGAGGAGTGTGATTCGCGTGGATCTTTAATCTTGAA GAAGTATATGGAATATAGGAAATTGG[C/T]TCAGTTGT CCTCTGAAATCAATGCTCAAAACAAGAATTTGCTAGCT GTTGGTGGACCAGAAGGACCCGACCCTAGGGAAGTC GAGTTATACCTGGAAGAA (SEQ ID No: 9) |

Example 5: Validation of the Markers a) Analysis of Markers on the Full F2 Population:

In order to validate the SNPs that resulted from the Bulk segregation analysis (BSA), 13 SNPs described in table 3 (including the eight SNPs from table 2 and additional 5 SNPs spread on Chromosome 6), were genotyped on 129 individual F2 plants.

WmCSV resistance scores were conducted for relevant F3 families (resulted from the genotyped F2 plants). The screen was conducted according to the specifications in example 1. F3 families that segregated for the resistance indicated that the F2 genotype should carry heterozygote composition in the WmCSV locus.

b) DNA Isolation and Genotyping—

DNA was isolated from young leaves, using magnetic beads (NucleoMag® 96 Plant), according to the protocol of the manufacturer of the beads, Macherey-Nagel.

Genotyping was done using KASP™ technology.

c) Results

Associations between 13 polymorphic SNPs genotypes for 129 F2 individuals (table 3) with phenotypic data of their F3 families were done using Chi square analysis in JMP statistical software (www.jmp.com). Results which are specified in table 4, indicate that markers 1-8 have high association ($0.88>R^2>0.92$) to the resistance while the other markers has low to no association to the resistance ($0.19>R^2>0.002$).

| | F2 genotyping-SNPs sequences and location | |
|---|---|---|
| SNP no | location on chr. 6 | Sequence |
| #1 | 880 855 | SEQ ID No: 1, see table 2 |
| #2 | 1 611 911 | SEQ ID No: 2, see table 2 |
| #3 | 2 250 215 | SEQ ID No: 3, see table 2 |
| #4 | 3 914 695 | SEQ ID No: 4, see table 2 |
| #5 | 3 924 533 | SEQ ID No: 5, see table 2 |
| #6 | 3 925 779 | SEQ ID No: 6, see table 2 |
| #7 | 3 928 953 | SEQ ID No: 7, see table 2 |
| #9 | 3 971 181 | SEQ ID No: 9, see table 2 |
| #10 | 4 856 351 | CTACAGTTTCCTCATTTCTAAACTTTACCCACCACAAAACAAAGCC ACTACTGCAAGAAACTGTAATAATTAGAGGGGGGAGGTAAGGAAT TTGGTGGTA[T/A]GTTGGGGAAGCTCAAAATAGACTTCTGGTGAAT AGAATAGAACATAAATGAAGCCAATTTCTCAGACAAATCAACATTG AGTTTCCAAATCAAACACAAA (SEQ ID No: 10) |
| #11 | 10 238 387 | TTCAATAAATCTTGAAAATAGTTACTACAAGTAGTTTATTTATTATT TTGGAAACACACTCATAAGTGTATTTTATATTATTTTAATATGTGGG ATGGGG[A/G]CATTGAACCTCAAGCCTCTAGATTGATAGTTCACG TTCATGCCAGTTGAGCTATTACTCGTATTTGGATTTTGGTTTTGGC CTTGTAATTTTTGTTTGTA (SEQ ID No: 11) |
| #12 | 16 778 454 | TTATTGGCTAAAGGAGGATTATCAATTTCAAGTGCTGTTGAATGGA CTTCTAAAGGATCCACCATTTTCTTTTTCTGAGGAAGAGAGGAGC ATCATTCAT[T/C]ACCGTGTGAACGGGAGAAAGGAGGCTTGTCTG GTTGTCACAAAAGGCGTTCCCACCATTTGAGATGTTCTTTTCAATG ATTACATTCTCTTTCTCACTGA (SEQ ID No: 12) |
| #13 | 18 948 201 | ACCCCCTGCCGAACAGTATGATGTCCGAGCGGTGATGACGGGG GACGGCAGACGGCGGACAGAACCGCGAGGGCTGAACACGAACG |

-continued

F2 genotyping-SNPs sequences and location

| SNP no | location on chr. 6 | Sequence |
|---|---|---|
| | | CGACTCCGGCGAAC[T/A]GAGGAAAGCGACAGACGGTTGCAAAA ACGAGAGAGAGGGAGATGGAATCGGGCGACTTGCGTGAAGTTG GGATGGAGGGCGTGAACTGCAACCATTTAAA (SEQ ID No: 13) |
| #14 | 23 664 030 | CCAGTATTTCTTTACTTATTACCTGCAGGTGAAACTTAAGAATATG TTGTATCACACTGCTCGGATAAATTGTCTTGCTTGGTCTCCTGATA ACACCAAG[A/G]TTGCAACTGGTTCATTAGATACATGTGTTATCAT ATATGAAATTGACAAGCCAGCATCCAGTCGTCTAACAATAAAGGG AGCTCATTTGGGTGGGGTGTA (SEQ ID No: 8) |

TABLE 4

SNPs physical location on watermelon Chromosome 6 and genetic distance from WmCSV resistance.

| No | Genome position (Chr. 6) | $R^2$ |
|---|---|---|
| #1 | 880,855 | 0.88 |
| #2 | 1,611,911 | 0.92 |
| #3 | 2,250,215 | 0.92 |
| #4 | 3,914,695 | 0.92 |
| #5 | 3,924,533 | 0.92 |
| #6 | 3,925,779 | 0.92 |
| #7 | 3,928,953 | 0.83 |
| #9 | 3,971,181 | 0.92 |
| #10 | 4,856,351 | 0.19 |
| #11 | 10,238,387 | 0.005 |
| #12 | 16,778,454 | 0.005 |
| #13 | 18,948,201 | 0.0025 |
| #14 | 23,664,030 | 0.01 |

Example 6: Analysis of Markers on Advanced Breeding Lines for Resistance to WmCSV 277 watermelon (*Citrullus lanatus*) plants from 23 advanced breeding lines, originating from the same initial source (i.e. these breeding lines were obtained in different breeding programs, wherein the COLO1 introgression partner was used in all of them but different elite lines were used), were screened for WmCSV resistance using the protocol described in example 1.

DNA was extracted from all plants, and genotyped for the SNP markers described in table 2.

a) DNA Isolation and Genotyping

DNA was isolated from young leaves, using magnetic beads protocol of 'Machery-Nagel'. Genotyping was done using KASPar technology.

b) Results

Within the breeding lines only two markers segregated in close linkage to WmCSV resistance (described in table 5), SNP #3 and SNP#9. These markers predicted the trait in 21 out of the 22 lines screened (Predictive value of 95%).

The other markers, located on the physical map between the two markers, were linked to the trait but with lower predictive value of 60%. As mentioned above, the respective positions of the markers may however be subjected to modifications with further versions of the genome assembly of *C. lanatus*.

Genotyping results (table 5) show clearly that there is a strong association between WmCSV resistance and the SNP markers shown in table 5.

The plants in the F2 population (genotyped in example 6) underwent only one recombination event, a fact that is responsible for a high LD through a long chromosome segments. The breeding lines, on the contrary, are of advanced generations (F8, F9), therefore had several recombination events, and have a shorter LD. For this reason markers that were obtained in F2 may no longer be linked to the trait in a breeding line. In this study, the inventors were able to confirm the linkage of the markers obtained in the F2 generation also on advanced breeding lines. Using these markers in the breeding process will enable a person skilled in the art, to distinguish between resistant and susceptible plants using the markers described in table 5.

TABLE 5

Results of markers screen on watermelon advanced breeding lines

| Line number | WmCSV score | Number of plants | SNP allele Chr6_2250215_C->T | Chr6_3971181_C->T |
|---|---|---|---|---|
| 1 | R | 9 | C | C |
| 2 | R | 10 | C | C |
| 3 | R | 13 | C | C |
| 4 | S | 12 | T | T |
| 5 | S | 9 | Segregating | segregating |
| 6 | S | 17 | T | T |
| 7 | R | 7 | C | C |
| 8 | R | 6 | C | C |
| 9 | S | 12 | T | T |
| 10 | R | 7 | C | C |
| 11 | S | 13 | T | T |
| 12 | S | 11 | T | T |
| 13 | R | 6 | C | C |
| segregating | S | 4 | T | T |
| 14 | R | 6 | C | C |
| 16 | R | 5 | C | C |

TABLE 5-continued

Results of markers screen on watermelon advanced breeding lines

| Line number | WmCSV score | Number of plants | SNP allele Chr6_2250215_C->T | Chr6_3971181_C->T |
|---|---|---|---|---|
| 17 | S | 20 | T | T |
| 18 | S | 27 | T | T |
| 19 | R | 11 | C | C |
| 20 | S | 15 | T | T |
| 21 | R | 10 | C | C |
| 22 | S | 16 | T | T |
| 23 | S | 15 | T | T |

Example 7: SLCV Inoculation and Disease Screening

Squash Leaf Curl Virus (SLCV) is caused by a whitefly transmitted geminivirus with geminate particles, 22*38 nm. The circular ssDNA genome is bipartite and consists of two similar-sized species. Known hosts are in the Cucurbitaceae, Leguminosae, Solanaceae and Euphorbiaceae. The virus is transmitted by the whitefly, Bemisia tabaci, especially biotype B, and by mechanical inoculation with sap. The development of phenotyping system requires the establishment of the following aspects that have to be validated for repeatability and reliability: virus growth and maintenance, vector growth and maintenance, inoculation and scoring methodologies.

Virus Growth and Maintenance

The Squash Leaf Curl Virus was maintained in isolated infected squash plants (Cucurbita pepo) grown in an insect-proof greenhouse. Cultures of the SLCV isolate were maintained on Squash Leaf Curl Virus susceptible squash plants (Cucurbita pepo) 'Maayan' (Hazera Genetics Ltd, now Hazera Seeds Ltd).

Whitefly Maintenance and Inoculation of Plants

Whitefly (B. tabaci, biotype B) colonies were reared on cotton (Gossypium hirsutum L.) plants grown in muslin-covered cages maintained inside an insect-proof greenhouse with natural lighting and temperature control (26° C. during the day and 20° C. during the night). Adult whiteflies were provided a 48-h acquisition access period on SLCV infected squash source plants (Cucurbita pepo) 'Maayan'.

Inoculation of Plants

The acquisition access period was followed by a 48-h inoculation access period on watermelon (Citrullus lanatus) plants to be tested for resistance to SLCV, said plants being at the two true leaves development level. Following the inoculation access period, the whiteflies were removed by treating plants with imidacloprid (Confidor; Bayer, Leverkusen, Germany). The plants were kept in the greenhouse (insect-proof greenhouse with natural lighting and temperature control: 26° C. during the day and 20° C. during the night, during spring season (April-June), for a four weeks incubation period.

Disease Screening

The development of symptoms is followed and registered up to 30 days post inoculation (DPI) using two levels, resistant and susceptible, on individual plant basis. SLCV causes severe systemic stunting and leaf curl on susceptible plants. Five lines are tested, two according to the invention that are known to be resistant to WmCSV and three that are known to be susceptible to WmCSV.

| Line | WmCSV | SLCV resistant plants | SLCV susceptible plants |
|---|---|---|---|
| 1 | Resistant | 26 plants | 2 plants |
| 2 | Resistant | 32 plants | 0 plants |
| 3 | Susceptible | 15 plants | 17 plants |
| 4 | Susceptible | 13 plants | 19 plants |
| 5 | Susceptible | 23 plants | 8 plants |

As can be deduced from the above results, C. lanatus plants according to the invention, derived from the deposited seeds, are not only resistant to WmCSV infections, but are also resistant to SLCV infection.

Example 8: Protocol for Obtaining Seedless Watermelon Fruits

Triploid watermelons are generally created by
1) crossing a tetraploid (4×) female parent line with diploid (2×) male parent line.
2) The resulting triploid (3×) watermelon seeds or plants are planted in a field with diploid (2×) watermelon pollenizers.

The resulting fruit of the triploid watermelon are seedless.

The tetraploid female watermelon line (needed at step 1) is generally obtained from a diploid inbred line, using generally chemicals that alter mitosis of a diploid inbred line, in order to obtain plants with unusual numbers of chromosomes. For example, colchicine is a chemical known for many years as altering the mitotic spindle fibers of diploid cells resulting in a number of cells that are tetraploid. The diploid line used to create a tetraploid is selected based on the traits desired for the tetraploid line, as such traits are generally maintained through the doubling of chromosomes.

It usually requires at least two generations of self-pollination and selection to "fix" the 4× condition, after the chemical (generally colchicines) treatment generation because, often, chromosomal aberrations are encountered that affect seed fertility, and must be eliminated. Once the stable tetraploid containing the desired characteristics is verified, it then can be used as a stable female parent for the production of the triploid hybrid. A stable diploid inbred is selected for use as the male parent. Methods for developing tetraploid plants are described inter alia in Kihara, H., 1951 and Eigsti, 1971.

Traits that are desired for a tetraploid line, and/or for the triploid seeds, may therefore first be introgressed into the diploid inbred lines that will be used to develop the tetraploid lines by breeding methods well known to those skilled in the art.

The tetraploid female parent line and diploid male parent line are planted in a seed production field. The pollen of the diploid male parent is transferred to the female tetraploid flower by methods well known to those skilled in the art. The resulting fruit contain triploid seeds which are planted to produce the triploid plants.

The seedless condition in triploid watermelon is the result of the presence of three homologous sets of chromosomes per somatic cell rather than the usual two. Cells with three sets of homologous chromosomes are said to be triploid and are designated as 3×. The triploid seedless watermelons have 33 chromosomes (2N=3×=33) in their somatic cells. The inability of the triploid zygote to produce normal viable gametes (pollen and egg cells) causes the absence of seeds in triploid fruits.

Adequate viable pollen supply from the diploid pollenizer watermelon is essential for the triploid female flowers to set and develop into regular seedless fruit. The female flowers of triploid watermelon will not set if they are not pollinated by viable pollen of diploid watermelon. The diploid watermelon grown in a field of triploid plants is referred to herein as the "pollenizer."

It is thus essential to have diploid watermelon lines resistant to geminiviruses, either for giving rise to tetraploid plants or for crossing with tetraploid plants, tetraploid plants resistant to geminiviruses, triploid plants resistant to geminiviruses as well as diploid "pollenizer" watermelon plants resistant to geminiviruses, as all these plants are likely to be infected by geminiviruses in the process of obtaining seedless watermelons.

Example 9: Use of a Marker Linked to Resistance in Breeding Programs

A study has been carried out to confirm that the selection based on the SNP markers linked to geminiviruses resistance according to the invention, and especially SNP#3, can be implemented in breeding watermelons resistant to geminiviruses.

The study has been conducted on six different F2 populations, each F2 arising from a cross between a resistant *C. lanatus* line and a susceptible *C. lanatus* line, the resulting F1 being then selfed. The resistant lines used in this study are 6 different resistant lines, all arising from an initial interspecific cross between a *Citrullus colocynthis* (COLO1) plant (see example 2), and thus comprising in their genome introgressed sequences from *Citrullus colocynthis* conferring resistance to geminiviruses, located on chromosome 6, between SNP#10 and the telomere adjacent to SNP#1.

All the F2 plants (187 individuals per F2 population) were genotyped with the marker corresponding to SNP#3.

Several F2 plants, identified as resistant according to the marker score, i.e. homozygous for allele C of SNP#3, were selfed in order to get the F3 seeds (number of plants per F2 population is shown in table 6), giving rise to a F3 family. These F3 families (total of 75 families), were phenotyped for resistance to WmCSV (22 plants per family have been tested). F2 marker results and F3 phenotype results are shown in table 6.

Out of 75 F3 families tested, only one gives rise to plants which do not match the F2 marker prediction, i.e. gives rise to plants which are segregating with respect to the resistance trait, although the F2 parent of this family was genotyped as homozygous for SNP#3.

For the 74 other F3 families, all the 22 individual plants of these families were uniformly resistant to WmCSV. Therefore, the expected phenotype was fully matched with the genotype in 74 out of 75 F3 families. It can thus be concluded that the marker corresponding to SNP#3 has more than 98% predictability of resistant plants in F2 population, as a marker of resistance to WmCSV.

TABLE 6

| No F2 population | No F3 families | Phytopathology result | Marker result | Remarks |
|---|---|---|---|---|
| 1 | 21 | R | R | |
| 2 | 12 | R | R | |
| 3 | 13 | R* | R | *one F3 family is segregating |
| 4 | 11 | R | R | |
| 5 | 8 | R | R | |
| 6 | 10 | R | R | |
| Total | 75 | | | |

R = resistant, according to the phytopathology test or according to the genotyping test based on SNP#3.

REFERENCES

Abudy, A., Sufrin-Ringwald, T., Dayan-Glick, C., Guenoune-Gelbart, D., Livneh, O., Zaccai, M., and Lapidot, M. 2010. Watermelon chlorotic stunt and Squash leaf curl begomoviruses—new threats to cucurbit crops in the Middle East. Israel J. Plant Sci. 58:33-42.

Al-Musa, A.; Anfoka, G.; Al-Abdulat, A.; Misbeh, S.; Haj Ahmed, F.; Otri, I. Watermelon chlorotic stunt virus (WmCSV) 2011. A serious disease threatening watermelon production in Jordan. Virus Genes 43, 79-89.

Bananej, K., Ahoonmanesh, A., and Kheyr-Pour, A. 2002. Host range of an Iranian isolate of Watermelon chlorotic stunt virus as determined by whitefly-mediated inoculation and agroinfection, and its geographical distribution. J. Phytopathol. 150:423-430.

Bedford, I. D., Briddon, R. W., Jones, P., Al-Kaff, N., Markham, P. G. 1994. Differentiation of three whitefly-transmitted geminiviruses from the Republic of Yemen. European Journal of Plant Pathology 100: 243-257.

Bumgarner and Matthew Kleinhenz, 2012. "Using Brix as an indicator of Vegetable Quality: Instructions for measuring Brix in Cucumber, Leafy Greens, Sweet Corn, Tomato and Watermelon" H&CS department OSU HYG-1653-12.

Davis A. R. et al, 2007. Evaluation of Watermelon and Related Species for Resistance to Race 1W Powdery Mildew. J. Amer. Soc. Hort. Sci. 132(6):790-795.

Eigsti, O. J., 1971, Seedless Triploids, HortScience 6, pgs. 1-2.

Fauquet, C. M., Briddon, R. W., Brown, J. K., Moriones, E., Stanley, J., Zerbini, M., and Zhou, X., 2008. Geminivirus strain demarcation and nomenclature. Arch. Virol. 153: 783-821.

Funayama, S. 2001. Effects of Virus Infection and Light Environment on Population Dynamics of *Eupatorium makinoi* (Asteraceae). American Journal of Botany 88: 616

Jones, P., Sattar, M. H. A., Al-Kaff, N. 1988. The incidence of virus disease in watermelon and sweet melon crops in the Peoples Republic of Yemen and its impact on cropping policy. Aspects of Applied Biology 17: 203-207

Jones, D. R. 2003. Plant viruses transmitted by whiteflies. Eur. J. Plant Pathol. 109:195-219.

Kihara, H., 1951, Triploid Watermelons, Proceedings of American Society for Horticultural Science 58:217-230;

Lapidot, M., and Friedmann, M. 2002. Breeding for resistance to whitefly-transmitted geminiviruses. Ann. Appl. Biol. 140:109-127.

Larson et al., 2000. Florida Crop/Pest Management Profile: Watermelon. Agronomy, Florida Cooperative Extension Service CIR1236.

Lecoq, H., G. A. Dafalla, Y. F. Mohamed, H. M. Ali, C. Wipf-Scheibel, C. Desbiez, A. E. Eljack, S. K. Omara, and M. Pitrat, 1994. Survey of virus diseases infecting cucurbit crops in Eastern, Central and Western Sudan. Khartoum Univ. J. Agric. Sci. 2, 67-82.

Marchelo, P. W. (1996). Studies on the Epidemiology of Watermelon Chlorotic Stunt Geminivirus (WCSV) on watermelon Citrullus lanatus (Thunb) in central Sudan. M. Sc. University of Gezira. 87 pp.

M. S. Ali-Shtayeh, R. M. Jamous, E. Y. Hussein, O. B. Mallah, and S. Y. Abu-Zaitoun. 2012. First Report of Watermelon chlorotic stunt virus in Watermelon in the Palestinian Authority. The American Phytopathological Society. Volume 96, Number 1 Page 149.

Prowidenti, 1993. "Resistance to viral disease of cucurbits", In Kyle, M. M., ed. Resistance to viral diseases of vegetables, Portland, Oreg., Timber Press, 1993:8-43

Raaed M. Mohamed Elhassan, Sadig K. Omara, Gasim A. Dfalla, Mohamed T. Yousif, Ali E. El-jack. 2008. Evaluation of Watermelon (Citrullus spp.) germplasm for resistance to Watermelon Chlorotic Stunt Virus. Sudan Journal of Agricultural Research Vol. 12 PP. 87-94.

Samsatly, J.; Sobh, H.; Jawhari, M.; Najjar, C.; Haidar, A.; Abou-Jawdah, Y. 2012. First report of Watermelon chlorotic stunt virus in cucurbits in Lebanon. Plant Disease Vol. 96 PP. 1703.

Smyth, G. K., 2004. Linear models and empirical Bayes methods for assessing differential expression in microarray experiments. Statistical Applications in Genetics and Molecular Biology 3, No. 1, Article 3.

Tetteh A. Y. et al, 2010. Identifying resistance to powdery mildew race 2W in the USDA-ARS Watermelon germplasm collection. Crop Science, Vol. 50, 933-939.

Tetteh, A. Y. et al, 2013. Inheritance of Resistance to the New Race of Powdery Mildew in Watermelon. Crop Science, Vol. 53, 880-887.

Walkey, D. G. A., Alhubaishi, A. A., Webb, M. J. W. 1990. Plant virus diseases in the Yemen Arab Republic. Tropical Pest Management 36: 195-206.

Wein, H. C. 1997. "The Cucurbits: Cucumber, Melon, Squash and Pumpkin" The Physiology of Vegetable Crops. CAB International Ch. 9

Yang, Y. H., Dudoit, S., Luu, P., Lin, D. M., Peng, V., Ngai, J., and Speed, T. P. (2002). Normalization for cDNA microarray data: a robust composite method addressing single and multiple slide systematic variation. Nucleic Acids Research 30(4):e15.

Yang, Y. H., and Thorne, N. P. (2003). Normalization for two-color cDNA microarray data. In: D. R. Goldstein (ed.), Science and Statistics: A Festschrift for Terry Speed, IMS Lecture Notes—Monograph Series, Volume 40, pp. 403-418;

Yousif, M, T., Kheyr-Pour, A., Gronenborn, B., Pitrat, M., Dogimont, C. 2007. Sources of resistance to Watermelon Chlorotic Stunt Virus in melon. Plant Breeding 126: 422-427.

What is claimed is:

1. A *Citrullus lanatus* seed having in its genome introgressed sequences from *Citrullus colocynthis* conferring resistance to geminiviruses only when present homozygously,
wherein said introgressed sequences are located on homologous chromosome 6, within the chromosomal region delimited by telomere and SNP#10 (SEQ ID No:10) and comprising SNP#1 (SEQ ID N:1) and are chosen from the introgressed sequences from *C. colocynthis* present in the genome of a seed *Citrullus lanatus*—WMCSVR, deposited at NCIMB accession number NCIMB-42197, on chromosome 6.

2. The *C. lanatus* seed according to claim 1, wherein said introgressed sequences are located at one or more of the following loci:
locus encompassing SNP#3 (SEQ ID No:3); and/or
locus encompassing SNP#9 (SEQ ID No:9).

3. The *C. lanatus* seed according to claim 1, wherein said introgressed sequences are in linkage disequilibrium with allele C of SNP#3 (SEQ ID No:3) and/or with allele C of SNP#9 (SEQ ID No:9), preferably with a positive linkage disequilibrium.

4. The *C. lanatus* seed according to claim 1, wherein said introgressed sequences are located in its genome at less than 20 cM, preferably less than 15 cM, preferably less than 10 cM, preferably less than 5 cM of the locus corresponding to SNP#3 (SEQ ID No:3).

5. The *C. lanatus* seed according to claim 1, wherein said introgressed sequences are located in its genome at less than 20 cM, preferably less than 15 cM, preferably less than 10 cM, preferably less than 5 cM of the locus corresponding to SNP#9 (SEQ ID No:9).

6. The *C. lanatus* seed according to claim 1, wherein the presence of said introgressed sequences on each allele of chromosome 6 is characterized by:
the presence of allele C of SNP#3 (SEQ ID No:3), and the absence of allele T for said SNP; and/or
the presence of allele C of SNP#9 (SEQ ID No:9), and the absence of allele T for said SNP.

7. The *C. lanatus* seed according to claim 1, wherein said introgressed sequences are located within the chromosomal interval defined by SNP#1 (SEQ ID No:1) and SNP#10 (SEQ ID No:10) on chromosome 6.

8. The *C. lanatus* seed according to claim 1, wherein said resistance is a resistance to begomoviruses.

9. The *C. lanatus* seed according to claim 8, wherein the *begomovirus* is Watermelon Chlorotic Stunt Virus (WmCSV) or Squash Leaf Curl Virus (SCLV).

10. The *C. lanatus* seed according to claim 1, wherein said seed is diploid, triploid, tetraploid and/or allopolyploid.

11. A *C. lanatus* plant resistant to geminiviruses grown from a seed according to claim 1.

12. A hybrid plant of *C. lanatus*, obtained by crossing a plant resistant to geminiviruses according to claim 11 with a susceptible plant of *C. lanatus*.

13. A plant or plant parts of *C. lanatus* having in its genome introgressed sequences from *C. colocynthis* conferring resistance to geminiviruses only when present homozygously, wherein said plant or plant part is obtained from a seed according to claim 1.

14. A cell of a *C. lanatus* plant according to claim 11, comprising in its genome introgressed sequences from *C. colocynthis* on chromosome 6 conferring resistance to geminiviruses only when present homozygously.

15. A tissue culture of regenerable cells of the plant according to claim 11, wherein the regenerable cells are derived from embryos, protoplasts, meristematic cells, callus, pollen, leaves, anthers, stems, petioles, roots, root tips, fruits, seeds, flowers, cotyledons, and/or hypocotyls, and contain in their genome introgressed sequences from *C. colocynthis* on chromosome 6 conferring resistance to geminiviruses only when present homozygously.

16. A method for detecting and/or selecting *C. lanatus* plants having introgressed sequences from *C. colocynthis*, said introgressed sequences conferring resistance to geminiviruses only when present homozygously, comprising detection of at least one of the following markers: allele C of SNP#3 (SEQ ID No:3) and allele C of SNP#9 (SEQ ID No:9), in a genetic material sample of the plant to be selected.

17. A method for the production of *C. lanatus* plants resistant to geminiviruses, comprising the steps of:
a) crossing a plant grown from the seed according to claim 1 and a susceptible or less resistant *C. lanatus* plant,
b) selecting a plant in the progeny thus obtained bearing sequences conferring resistance to geminiviruses only when present homozygously;
c) self-pollinating one or several times the plant obtained at step b) and selecting a resistant plant in the progeny thus obtained;
wherein SNPs markers are used in steps b) and c) for selecting plants bearing sequences conferring resistance to geminiviruses only when present homozygously and/or plants resistant to geminiviruses.

18. A method for the production of *C. lanatus* plants resistant to geminiviruses comprising the steps of:
a1) crossing a plant corresponding to the seed according to claim 1 and a susceptible or less resistant *C. lanatus* plant, thus generating the F1 population,
a2) advancing the F1 population to create F2 population,
b) selecting resistant individuals in the progeny thus obtained;
c) optionally self-pollinating one or several times the resistant plant obtained at step b) and selecting a resistant plant in the progeny thus obtained;
d) optionally backcrossing the resistant plant selected in step b) or c) with a *C. lanatus* plant susceptible to geminivirus infection,
e) selecting in the progeny a plant bearing sequences linked to the resistance to geminiviruses,
f) self-pollinating the plant obtained at step e) or crossing distinct plants obtained at step e), one or several times, and
g) selecting a plant resistant to geminiviruses,
wherein SNPs markers are used for selecting plants bearing the introgressed sequences linked to resistance to geminiviruses only when present homozygously or for selecting plants resistant to geminiviruses.

19. A method for breeding *C. lanatus* plants resistant to geminiviruses, comprising the steps of crossing a plant grown from the deposited seeds NCIMB 42197, with a *C. lanatus* plant.

20. The method according to claim 17, wherein the selection is carried out by detection of at least one of the following alleles: allele C of SNP#3 (SEQ ID No:3) or allele C of SNP#9 (SEQ ID No:9).

21. A *C. lanatus* plant obtained by the method according to claim 19.

22. The method according to claim 18, wherein the selection is carried out by detection of at least one of the following alleles: allele C of SNP#3 (SEQ ID No:3) or allele C of SNP#9 (SEQ ID No:9).

23. The plant part according to claim 13, wherein said plant part is explant, scion, cutting, seed, fruit, rootstock, pollen or ovule.

* * * * *

```
                               SEQUENCE LISTING

<160> NUMBER OF SEQ ID NOS: 26

<210> SEQ ID NO 1
<211> LENGTH: 201
<212> TYPE: DNA
<213> ORGANISM: Citrullus lanatus

<400> SEQUENCE: 1
ttcacaccaa atccatcctc atcttagcaa aacatcatag gcaccaattt tgtttgaagt      60
taaaatacca ttttcatcca tgtaggattc attcaaattt mgtcacaaaa ctctcaaacg     120
tacaatttta gtcatgttct ttcctaaatt tcaaaagtag tccttttttgg ttagtttgag    180 gttaatattt ttttatatta a                                              201

<210> SEQ ID NO 2
<211> LENGTH: 201
<212> TYPE: DNA
<213> ORGANISM: Citrullus lanatus

<400> SEQUENCE: 2
aaactggctt cactatcatc gtccaccact aattgtggaa ttttcagcac ccctttttg       60 gagtcaaaac tcacgtcagt aaggctcttt gtgccgcttt sctggaaatc tatccccgcg    120
tcacgaagct gtgttgcatg tcgaatcact tgatattctg gcccggattt cttcgttttt    180
ctctccatac taccatcctt a                                              201

<210> SEQ ID NO 3
<211> LENGTH: 201
<212> TYPE: DNA
<213> ORGANISM: Citrullus lanatus

<400> SEQUENCE: 3
```

```
tgattctgtt tgttttgcta actccaggac ttctctttca gcttcccgga aatcgcaggt    60
gcttagagtt tggcaacttt cacacgagtg ctgcttctat yatcgtccat tcgattctct   120
acttcggtct catttgcgtc ttcttactcg ccatcaaggt tcatctctac atcggttcct   180
aatatgactt gctccgatgc c                                             201
```

```
<210> SEQ ID NO 4
<211> LENGTH: 201
<212> TYPE: DNA
<213> ORGANISM: Citrullus lanatus

<400> SEQUENCE: 4
tcttcttctg gctatgtatc tgttggtgtt aatacttatc ttgagcccaa tgtagttttg    60
gacgactgcc ttgttcttaa ccttccggac ttctatttct yatatactgt atgaatggtt   120
atctgttaaa tttgtcagta tgatatgatt ttgacatgac atgttttggc tctttccact   180
tctcgttttt cttggctaca t                                             201
```

```
<210> SEQ ID NO 5
<211> LENGTH: 201
<212> TYPE: DNA
<213> ORGANISM: Citrullus lanatus

<400> SEQUENCE: 5
tgatatagaa tgatattacg atgcaatata agttaagaga acatataaga ttcgtttgtt    60
ttatatttca caattacccc tttaaatgaa ggcacaaact scctgaaagc acatgagtca   120
tttagtttaa cttgcgcagg tacacaattt gtgttttcc aagaaaaggg gttggcctct    180
tgtgataggg taaatacttc g                                             201
```

```
<210> SEQ ID NO 6
<211> LENGTH: 201
<212> TYPE: DNA
<213> ORGANISM: Citrullus lanatus

<400> SEQUENCE: 6
aataggatgt ggccaagaga ttcccctgcc ttgttacaca atggacaaac ggtggcatga    60
gagactgaga tggaagttct ttccggttgt cagctaaatt saggttcacg attcacacca   120
aaatatttgt tttcttaggg ctcttggttt tccaaattgc attaaagatg ctgcagacca   180
gattggaaaa agcagcaaat g                                             201
```

```
<210> SEQ ID NO 7
<211> LENGTH: 201
<212> TYPE: DNA
<213> ORGANISM: Citrullus lanatus

<400> SEQUENCE: 7
ccttatggct tctatgcctg atatacatca agctgtagag ttttaagta ccacaattgt    60 ggggataggg attgaacttc ccacctcaag gatagaaggt ygtgccaatc accactgagc   120
ttacctcgat ttggccatca agctgtagag ttgctcacgc aagaaaggg gaaaaccagc   180 actgccaatg tccaaaaaca g                                             201
```

```
<210> SEQ ID NO 8
<211> LENGTH: 201
<212> TYPE: DNA
<213> ORGANISM: Citrullus lanatus
```

<400> SEQUENCE: 8

```
ccagtatttc tttacttatt acctgcaggt gaaacttaag aatatgttgt atcacactgc    60
tcggataaat tgtcttgctt ggtctcctga taacaccaag rttgcaactg gttcattaga   120
tacatgtgtt atcatatatg aaattgacaa gccagcatcc agtcgtctaa caataaaggg   180
agctcatttg ggtggggtgt a                                             201
```

<210> SEQ ID NO 9
<211> LENGTH: 201
<212> TYPE: DNA
<213> ORGANISM: Citrullus lanatus

<400> SEQUENCE: 9

```
ggtgaggatg ggattgttta cgcaatatgt gaacttcagg aggagtgtga ttcgcgtgga    60
tctttaatct tgaagaagta tatggaatat aggaaattgg ytcagttgtc ctctgaaatc   120
aatgctcaaa acaagaattt gctagctgtt ggtggaccag aaggacccga ccctagggaa   180
gtcgagttat acctggaaga a                                             201
```

<210> SEQ ID NO 10
<211> LENGTH: 201
<212> TYPE: DNA
<213> ORGANISM: Citrullus lanatus

<400> SEQUENCE: 10

```
ctacagtttc ctcatttcta aactttaccc accacaaaac aaagccacta ctgcaagaaa    60
ctgtaataat tagaggggggg aggtaaggaa tttggtggta wgttggggaa gctcaaaata   120
gacttctggt gaatagaata gaacataaat gaagccaatt tctcagacaa atcaacattg   180
agtttccaaa tcaaacacaa a                                             201
```

<210> SEQ ID NO 11
<211> LENGTH: 201
<212> TYPE: DNA
<213> ORGANISM: Citrullus lanatus

<400> SEQUENCE: 11

```
ttcaataaat cttgaaaata gttactacaa gtagtttatt tattatttg gaaacacact     60
cataagtgta ttttatatta ttttaatatg tgggatgggg rcattgaacc tcaagcctct   120
agattgatag ttcacgttca tgccagttga gctattactc gtatttggat tttggttttg   180
gccttgtaat ttttgtttgt a                                             201
```

<210> SEQ ID NO 12
<211> LENGTH: 201
<212> TYPE: DNA
<213> ORGANISM: Citrullus lanatus

<400> SEQUENCE: 12

```
ttattggcta aaggaggatt atcaatttca agtgctgttg aatggacttc taaaggatcc    60
accattttct ttttctgagg aagagaggag catcattcat yaccgtgtga acgggagaaa   120
ggaggcttgt ctggttgtca caaaaggcgt tcccaccatt tgagatgttc ttttcaatga   180
ttacattctc tttctcactg a                                             201
```

<210> SEQ ID NO 13
<211> LENGTH: 201
<212> TYPE: DNA
<213> ORGANISM: Citrullus lanatus

<400> SEQUENCE: 13
accccctgcc gaacagtatg atgtccgagc ggtgatgacg ggggacggca gacggcggac    60
agaaccgcga gggctgaaca cgaacgcgac tccggcgaac wgaggaaagc gacagacggt   120
tgcaaaaacg agagagaggg agatggaatc gggcgacttg cgtgaagttg ggatggaggg   180
cgtgaactgc aaccatttaa a                                             201

<210> SEQ ID NO 14
<211> LENGTH: 31
<212> TYPE: DNA
<213> ORGANISM: Citrullus lanatus

<400> SEQUENCE: 14
gattcattca aatttmgtca caaaactctc a                                   31

<210> SEQ ID NO 15
<211> LENGTH: 27
<212> TYPE: DNA
<213> ORGANISM: Citrullus lanatus

<400> SEQUENCE: 15
tttgtgccgc tttsctggaa atctatc                                        27

<210> SEQ ID NO 16
<211> LENGTH: 27
<212> TYPE: DNA
<213> ORGANISM: Citrullus lanatus

<400> SEQUENCE: 16
gtgctgcttc tatyatcgtc cattcga                                        27

<210> SEQ ID NO 17
<211> LENGTH: 31
<212> TYPE: DNA
<213> ORGANISM: Citrullus lanatus

<400> SEQUENCE: 17
cggacttcta tttctyatat actgtatgaa t                                   31

<210> SEQ ID NO 18
<211> LENGTH: 27
<212> TYPE: DNA
<213> ORGANISM: Citrullus lanatus

<400> SEQUENCE: 18
gaaggcacaa actscctgaa agcacat                                        27

<210> SEQ ID NO 19
<211> LENGTH: 27
<212> TYPE: DNA
<213> ORGANISM: Citrullus lanatus

<400> SEQUENCE: 19
tgtcagctaa attsaggttc acgattc                                        27

<210> SEQ ID NO 20
<211> LENGTH: 27
<212> TYPE: DNA
<213> ORGANISM: Citrullus lanatus

<400> SEQUENCE: 20

```
aaggatagaa ggtygtgcca atcacca                                  27

<210> SEQ ID NO 21
<211> LENGTH: 27
<212> TYPE: DNA
<213> ORGANISM: Citrullus lanatus

<400> SEQUENCE: 21
tataggaaat tggytcagtt gtcctct                                  27

<210> SEQ ID NO 22
<211> LENGTH: 27
<212> TYPE: DNA
<213> ORGANISM: Citrullus lanatus

<400> SEQUENCE: 22
gaatttggtg gtawgttggg gaagctc                                  27

<210> SEQ ID NO 23
<211> LENGTH: 23
<212> TYPE: DNA
<213> ORGANISM: Citrullus lanatus

<400> SEQUENCE: 23
gtgggatggg grcattgaac ctc                                      23

<210> SEQ ID NO 24
<211> LENGTH: 27
<212> TYPE: DNA
<213> ORGANISM: Citrullus lanatus

<400> SEQUENCE: 24
gagcatcatt catyaccgtg tgaacgg                                  27

<210> SEQ ID NO 25
<211> LENGTH: 23
<212> TYPE: DNA
<213> ORGANISM: Citrullus lanatus

<400> SEQUENCE: 25
ctccggcgaa cwgaggaaag cga                                      23

<210> SEQ ID NO 26
<211> LENGTH: 27
<212> TYPE: DNA
<213> ORGANISM: Citrullus lanatus

<400> SEQUENCE: 26
tgataacacc aagrttgcaa ctggttc                                  27
```